(12) United States Patent
Kaufman et al.

(10) Patent No.: US 12,326,492 B2
(45) Date of Patent: Jun. 10, 2025

(54) SYSTEMS AND METHODS OF DETECTING INTERSTITIAL CYSTITIS

(71) Applicant: LIPELLA PHARMACEUTICALS, INC., Pittsburgh, PA (US)

(72) Inventors: Jonathan Kaufman, Pittsburgh, PA (US); Michael B. Chancellor, Pittsburgh, PA (US)

(73) Assignee: LIPELLA PHARMACEUTICALS, INC., Pittsburgh, PA (US)

( * ) Notice: Subject to any disclaimer, the term of this patent is extended or adjusted under 35 U.S.C. 154(b) by 0 days.

(21) Appl. No.: 16/205,654

(22) Filed: Nov. 30, 2018

(65) Prior Publication Data

US 2019/0094323 A1    Mar. 28, 2019

Related U.S. Application Data

(63) Continuation of application No. 14/862,923, filed on Sep. 23, 2015, now abandoned, which is a continuation-in-part of application No. 14/678,638, filed on Apr. 3, 2015, now abandoned, and a continuation-in-part of application No. PCT/US2015/024309, filed on Apr. 3, 2015.

(60) Provisional application No. 62/062,339, filed on Oct. 10, 2014, provisional application No. 61/974,964, filed on Apr. 3, 2014.

(51) Int. Cl.
| | |
|---|---|
| *G01R 33/56* | (2006.01) |
| *A61B 5/00* | (2006.01) |
| *A61B 5/055* | (2006.01) |
| *A61K 49/00* | (2006.01) |
| *A61K 49/10* | (2006.01) |
| *A61K 49/18* | (2006.01) |

(52) U.S. Cl.
CPC ........ *G01R 33/5601* (2013.01); *A61B 5/0044* (2013.01); *A61B 5/055* (2013.01); *A61K 49/0004* (2013.01); *A61K 49/103* (2013.01); *A61K 49/105* (2013.01); *A61K 49/1827* (2013.01)

(58) Field of Classification Search
CPC ............ A61K 49/1827; A61K 49/0004; A61K 49/103; A61K 49/105; G01R 33/5601; A61B 5/055; A61B 5/0044
See application file for complete search history.

(56) References Cited

U.S. PATENT DOCUMENTS

| | | | |
|---|---|---|---|
| 5,888,986 A | 3/1999 | Morales et al. | |
| 7,063,860 B2 | 6/2006 | Chancellor et al. | |
| 7,368,099 B2 | 5/2008 | Katayama et al. | |
| 8,110,217 B2 | 2/2012 | Chancellor et al. | |
| 2002/0151787 A1* | 10/2002 | Bjornerud | A61K 49/1863 |
| | | | 600/420 |
| 2002/0168321 A1* | 11/2002 | Tournier | A61K 49/1818 |
| | | | 424/9.32 |
| 2007/0003610 A1 | 1/2007 | Chancellor et al. | |
| 2008/0206131 A1* | 8/2008 | Jaffray | A61K 49/0002 |
| | | | 424/9.1 |
| 2009/0130022 A1* | 5/2009 | Nishigaki | A61K 49/1812 |
| | | | 424/9.3 |
| 2010/0061938 A1 | 3/2010 | Fossheim et al. | |
| 2010/0104631 A1 | 4/2010 | Chancellor et al. | |
| 2010/0166739 A1 | 7/2010 | Chancellor et al. | |
| 2011/0200534 A1* | 8/2011 | Cheon | A61K 49/1836 |
| | | | 424/9.32 |
| 2015/0030667 A1 | 1/2015 | Kaufman et al. | |
| 2016/0045623 A1 | 2/2016 | Kaufman et al. | |
| 2016/0136306 A1 | 5/2016 | Kaufman et al. | |
| 2017/0189564 A9 | 7/2017 | Kaufman et al. | |

FOREIGN PATENT DOCUMENTS

| | | | | |
|---|---|---|---|---|
| WO | WO-9811922 A2 * | 3/1998 | ............. | A61K 49/06 |
| WO | 2003/015698 A2 | 2/2003 | | |
| WO | 2007/044748 A2 | 4/2007 | | |
| WO | 2009/139984 A2 | 11/2009 | | |
| WO | 2010/078403 A2 | 7/2010 | | |
| WO | 2015154007 A1 | 10/2015 | | |

OTHER PUBLICATIONS

Zhang et al., Biochem Biophys Res Commun., 2012, 524(4), p. 886-891. (Year: 2012).*
Unger, Magn. Res. Imaging, 1989, 7(4), p. 417-23. (Year: 1989).*
Avcu et al., Br. J. Radiol., 2011, 84(1006), p. 875-882. (Year: 2011).*
Beaumont et al., J. Cerebral Blood Flow and Metabolism, 2009, 29, p. 1714-1726. (Year: 2009).*
Hsiao et al., Investigative Radiology, 2009, 44(6), p. 329-335. (Year: 2009).*
Chelsky et al., J. Urology, 1994, 151(2), p. 346-349. (Year: 1994).*
Son et al. J. Bioactive and Compatible Polymers, 2011, 27(1), p. 54-66. (Year: 2011).*
Lee et al., Mag. Res. Imag., 2012, 30(6), p. 860-868. (Year: 2012).*
Bauer et al. "Theory of Contrast Agents in Magnetic Resonance Imaging: Coupling of Spin Relaxation and Transport" 1992, Magnetic Resonance in Medicine 26:16-39.
Goodman et al. The Pharmacological Basis of Therapeutics 1980, 6\super th\nosupersub ed., MacMillan Pub., New York (TOC).
Huang et al. "Improving the Magnetic Resonance Imaging Contrast and Detection Methods with Engineered Magnetic Nanoparticles" 2012, Theranostics 2(1):86-102.
International Search Report and Written Opinion for PCT/US2015/024309 dated Jul. 2, 2015.

(Continued)

*Primary Examiner* — Michael G. Hartley
*Assistant Examiner* — Leah H Schlientz
(74) *Attorney, Agent, or Firm* — Troutman Pepper Locke LLP (Rochester)

(57) ABSTRACT

The invention provides systems and methods for providing a diagnostic examination to a patient, including, but not limited to a determination of the permeability of a patients' body cavity.

40 Claims, 5 Drawing Sheets

(56) References Cited

OTHER PUBLICATIONS

Mohrs et al., Diagnosis of patent foramen ovale using contrast-enhanced dynamic MRI: a pilot study. American Journal of Roentgenology 184.1 (2005): 234-240.
Towner et al. "Contrast Enhanced Magnetic Resonance Imaging as a Diagnostic Tool to Assess Bladder Permeability and Associates Colon Cross Talk: Preclinical Studies in a Rat Model" Apr. 2015, J. Urology 193:1394-1400.
Wang et al. "Superparamagnetic Iron Oxide Based MRI Contrast Agents: Current Status of Clinical Application" 2011, Quantitative Imaging in Medicine and Surgery 1:35-40.
Weissig et al. "Long-Circulating Gadolinium-Loaded Liposomes: Potential Use for Magnetic Resonance Imaging of the Blood Pool" 2000, Colloids and Surfaces B: Biointerfaces 18:293-299.
Zhang et al. "Synergistic Enhancement of Iron Oxide Nonparticle and Gadolinium for Dual-Contrast MRI" Sep. 7, 2012, NIH Public Access Author Manuscript 425:886-891.
Zhou et al. "Gadolinium-Based Contrast Agents for MR Cancer Imaging" 2013, Wiley Interdisciplinary Reviews Nanomedicine and Nanobiotechnology 5:1-18.

\* cited by examiner

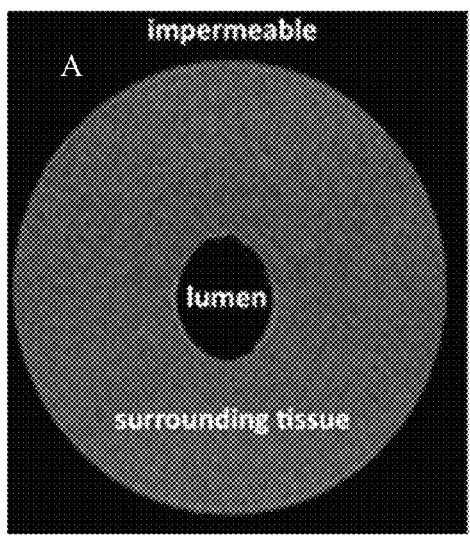 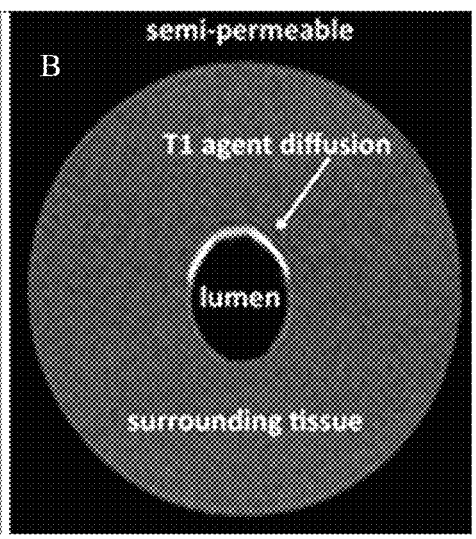
FIGURE 1A                    FIGURE 1B

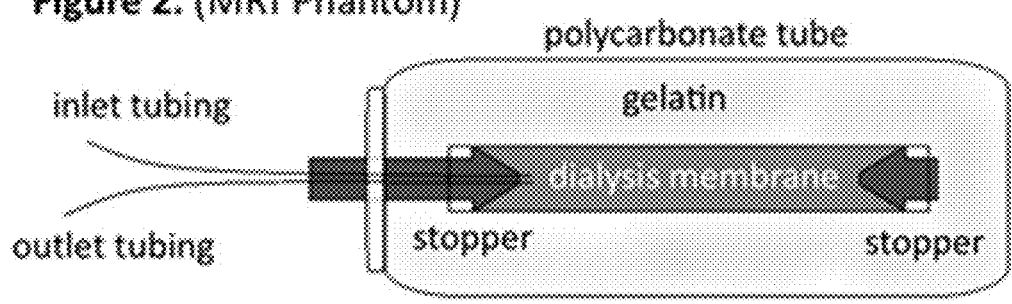
Figure 2. (MRI Phantom)

SYSTEMS AND METHODS OF DETECTING INTERSTITIAL CYSTITIS

CROSS-REFERENCE TO RELATED APPLICATIONS

This application is a continuation of U.S. application Ser. No. 14/862,923 entitled "Systems and Methods to Image Intercellular and Intercompartmental Defects with Magnetic Resonance Imaging (MRI)" filed Sep. 23, 2015, which is a continuation-in-part of PCT Application PCT/US2015/024309 entitled "Systems and Methods for detecting Interstitial cystitis" filed Apr. 3, 2015, which claims the benefit of U.S. Provisional Application Ser. No. 61/974,964 entitled "Systems and Methods of Detecting Interstitial Cystitis" filed Apr. 3, 2014, and U.S. Provisional Application Ser. No. 62/062,339 entitled "Systems and Methods of Detecting Interstitial Cystitis" filed Oct. 10, 2014; and a continuation-in-part of U.S. application Ser. No. 14/678,638 entitled "Systems and Methods for detecting Interstitial cystitis" filed Apr. 3, 2015, which claims the benefit of U.S. Provisional Application Ser. No. 61/974,964 entitled "Systems and Methods of Detecting Interstitial Cystitis" filed Apr. 3, 2014, and U.S. Provisional Application Ser. No. 62/062,339 entitled "Systems and Methods of Detecting Interstitial Cystitis" filed Oct. 10, 2014, each of which are hereby incorporated herein by reference in their entirety.

GOVERNMENT INTERESTS

Not Applicable

PARTIES TO A JOINT RESEARCH AGREEMENT

Brief Summary of the Invention

Embodiments herein are directed to methods for detecting patent foramen ovale in a patient comprising: administering a T1-reducing contrast agent and a T2-reducing contrast agent to the patient; and imaging the patient's heart; wherein diffusion of the T2 reducing contrast agent from the right atrium to the left atrium is indicative of patent foramen ovale.

Embodiments herein are directed to methods for measuring the permeability of a body cavity in a patient comprising: administering a T1-reducing contrast agent and a T2-reducing contrast agent to the patient; and imaging the patient; wherein diffusion of the T1 reducing contrast agent across the luminal surface of the body cavity is indicative of permeability. In some embodiments, the particle size of the T2-reducing contrast agent is larger than the particle size of the T1-reducing contrast agent. In some embodiments, the T1-reducing agent, the T2-reducing agent, or a combination thereof further comprises an aqueous solvent. In some embodiments, the T1-reducing contrast agent and the T2-reducing contrast agent are administered to the patient as a single composition; wherein the single composition comprises the T1-reducing contrast agent and the T2-reducing contrast agent. In some embodiments, the single composition further comprises an aqueous solvent. In some embodiments, the T1-reducing agent and the T2-reducing contrast agent are administered to the patient as two separate compositions; wherein a first composition comprises the T1-reducing contrast agent; and wherein a second composition comprises the T2-reducing contrast agent. In some embodiments, the two separate compositions each further comprise an aqueous solvent. In some embodiments, administering T1-reducing contrast agent and the T2-reducing contrast agent are completed simultaneously. In some embodiments, imaging the patient comprises imaging via magnetic resonance imaging. In some embodiments, imaging the patient is performed within about 10 minutes of administration of the T1-reducing contrast agent and the T2-reducing contrast agent. In some embodiments, the first T1-reducing contrast agent comprises a gadolinium compound. In some embodiments, the gadolinium compound is selected from gadopentetate dimeglumine (Gd-DTPA), gadoterate meglumine, gadoversetamide, gadoteridol, gadodiamide, gadobenate dimeglumine, gadobutrol, gadoxetate disodium, gadofosveset trisodium and combinations thereof. In some embodiments, the gadolinium compound is encapsulated in liposomes. In some embodiments, the T2-reducing contrast agent comprises an iron oxide. In some embodiments, the iron oxide is selected from iron (II) oxide, iron (III) oxide, ferumoxytol (Feraheme), Feraspin XS, Feraspin S, Feraspin M, Feraspin R, Feraspin L, Feraspin XL, iron nickel oxide nanopowder, iron oxide (II,III) magnetic nanoparticles, iron-nickel alloy nanopowder, magnetic iron oxide nanoparticles, carbon coated iron nanopowder, and combinations thereof. In some embodiments, the iron oxide is encapsulated in liposomes. In some embodiments, the patient's body cavity is selected from the urinary bladder, blood vessels, lymph vessels, coelom, pericardial cavity, pericardium, intraembryonic coelom, extraembryonic coelom, chorionic cavity, dorsal cavity, ventral cavity, thoracic cavity, abdominopelvic cavity, cranial cavity, spinal cavity (or vertebral cavity), a pleural cavity, superior mediastinum, thoracic cavity, abdominal cavity, pelvic cavity. abdominopelvic cavity, kidneys, ureters, stomach, intestines, liver, gallbladder, pancreas, anus, reproductive system and any combination thereof. In some embodiments, the patient's body cavity is the urinary bladder. In some embodiments, the patient is suspected of having interstitial cystitis, bladder pain syndrome or a combination thereof. In some embodiments, administration of the T1-reducing contrast agent and the T2-reducing contrast agent is achieved by instillation into the lumen of the urinary bladder.

In some embodiments, the particle size of the T2-reducing contrast agent is larger than the particle size of the T1-reducing contrast agent. In some embodiments, the T1-reducing agent, the T2-reducing agent, or a combination thereof further comprises an aqueous solvent. In some embodiments, the T1-reducing contrast agent and the T2-reducing contrast agent are administered to the patient as a single composition; wherein the single composition comprises the T1-reducing contrast agent and the T2-reducing contrast agent. In some embodiments, the single composition further comprises an aqueous solvent. In some embodiments, the T1-reducing agent and the T2-reducing contrast agent are administered to the patient as two separate compositions; wherein a first composition comprises the T1-reducing contrast agent; and wherein a second composition comprises the T2-reducing contrast agent. In some embodiments, the two separate compositions each further comprise an aqueous solvent. In some embodiments, administering T1-reducing contrast agent and the T2-reducing contrast agent are completed simultaneously.

Some embodiments are directed to methods for measuring the permeability of a body cavity in a patient comprising: imaging the patient after administering a T1-reducing contrast agent and a T2-reducing contrast agent to the patient; wherein diffusion of the T1 reducing contrast agent across the luminal surface of the body cavity is indicative of permeability. In some embodiments, the particle size of the T2-reducing contrast agent is larger than the particle size of the T1-reducing contrast agent. In some embodiments, the T1-reducing contrast agent and the T2-reducing contrast agent are administered to the patient as a single composition. In some embodiments, the single composition further comprises an aqueous solvent. In some embodiments, the T1-reducing contrast agent and the T2-reducing contrast agent are administered to the patient as two separate compositions; wherein a first composition comprises the T1-reducing contrast agent and a second composition comprises the T2-reducing agent. In some embodiments, the two separate compositions each further comprise an aqueous solvent. In some embodiments, administering T1-reducing contrast agent and the T2-reducing contrast agent are completed simultaneously. In some embodiments, imaging the patient comprises imaging via magnetic resonance imaging. In some embodiments, imaging the patient is performed within about 10 minutes of administration of the T1-reducing contrast agent and the T2-reducing contrast agent. In some embodiments, the first T1-reducing contrast agent comprises a gadolinium compound. In some embodiments, the gadolinium compound is selected from gadopentetate dimeglumine (Gd-DTPA), gadoterate meglumine, gadoversetamide, gadoteridol, gadodiamide, gadobenate dimeglumine, gadobutrol, gadoxetate disodium, gadofosveset trisodium and combinations thereof. In some embodiments, the gadolinium compound is encapsulated in liposomes. In some embodiments, the T2-reducing contrast agent comprises an iron oxide. In some embodiments, the iron oxide is selected from iron (II) oxide, iron (III) oxide, ferumoxytol (Feraheme), Feraspin XS, Feraspin S, Feraspin M, Feraspin R, Feraspin L, Feraspin XL, iron nickel oxide nanopowder, iron oxide (II,III) magnetic nanoparticles, iron-nickel alloy nanopowder, magnetic iron oxide nanoparticles, carbon coated iron nanopowder, and combinations thereof. In some embodiments, the iron oxide is encapsulated in liposomes. In some embodiments, the patient's body cavity is selected from the urinary bladder, blood vessels, lymph vessels, coelom, pericardial cavity, pericardium, intraembryonic coelom, extraembryonic coelom, chorionic cavity, dorsal cavity, ventral cavity, thoracic cavity, abdominopelvic cavity, cranial cavity, spinal cavity (or vertebral cavity), a pleural cavity, superior mediastinum, thoracic cavity, abdominal cavity, pelvic cavity. abdominopelvic cavity, kidneys, ureters, stomach, intestines, liver, gallbladder, pancreas, anus, reproductive system and any combination thereof. In some embodiments, the patient's body cavity is the urinary bladder. In some embodiments, the patient is suspected of having interstitial cystitis, bladder pain syndrome or a combination thereof. In some embodiments, administration of the T1-reducing contrast agent and the T2-reducing contrast agent is achieved by instillation into the lumen of the urinary bladder.

In some embodiments, imaging the patient's heart comprises imaging via magnetic resonance imaging. In some embodiments, imaging the patient's heart is performed within about 10 minutes of administration of the T1-reducing contrast agent and the T2-reducing contrast agent.

Some embodiments are directed to imaging compositions comprising: a T1-reducing contrast agent; and a T2-reducing contrast agent, wherein the T2-reducing contrast agent. In some embodiments, the imaging composition further comprises an aqueous solution. In some embodiments, the particle size of the T2-reducing contrast agent is larger than the particle size of the T1-reducing contrast agent. In some embodiments, the T1-reducing contrast agent comprises a gadolinium compound. In some embodiments, the gadolinium compound is selected from gadopentetate dimeglumine (Gd-DTPA), gadoterate meglumine, gadoversetamide, gadoteridol, gadodiamide, gadobenate dimeglumine, gadobutrol, gadoxetate disodium, gadofosveset trisodium and combinations thereof. In some embodiments, the gadolinium compound is encapsulated in liposomes. In some embodiments, the T2-reducing contrast agent comprises an iron oxide. In some embodiments, the iron oxide is selected from iron (II) oxide, iron (III) oxide, ferumoxytol (Feraheme), Feraspin XS, Feraspin S, Feraspin M, Feraspin R, Feraspin L, Feraspin XL, iron nickel oxide nanopowder, iron oxide (II,III) magnetic nanoparticles, iron-nickel alloy nanopowder, magnetic iron oxide nanoparticles, carbon coated iron nanopowder, and combinations thereof. In some embodiments, the iron oxide is encapsulated in liposomes.

In some embodiments, the first T1-reducing contrast agent comprises a gadolinium compound. In some embodiments, the gadolinium compound is selected from gadopentetate dimeglumine (Gd-DTPA), gadoterate meglumine, gadoversetamide, gadoteridol, gadodiamide, gadobenate dimeglumine, gadobutrol, gadoxetate disodium, gadofosveset trisodium and combinations thereof. In some embodiments, the gadolinium compound is encapsulated in liposomes.

In some embodiments, the T2-reducing contrast agent comprises an iron oxide. In some embodiments, the iron oxide is selected from iron (II) oxide, iron (III) oxide, ferumoxytol (Feraheme), Feraspin XS, Feraspin S, Feraspin M, Feraspin R, Feraspin L, Feraspin XL, iron nickel oxide nanopowder, iron oxide (II,III) magnetic nanoparticles, iron-nickel alloy nanopowder, magnetic iron oxide nanoparticles, carbon coated iron nanopowder, and combinations thereof.

In some embodiments, the iron oxide is encapsulated in liposomes. In some embodiments, administration of the T1-reducing contrast agent and the T2-reducing contrast agent is achieved by administration to the patient's cardiovascular system.

Some embodiments are directed to methods detecting patent foramen ovale in a patient comprising: imaging the patient after administering a T1-reducing contrast agent and a T2-reducing contrast agent to the patient; wherein diffusion of the T2 reducing contrast agent from the right atrium to the left atrium is indicative of patent foramen ovale.

In some embodiments, the particle size of the T2-reducing contrast agent is larger than the particle size of the T1-reducing contrast agent. In some embodiments, the T1-reducing agent, the T2-reducing agent, or a combination thereof further comprises an aqueous solvent.

In some embodiments, the T1-reducing contrast agent and the T2-reducing contrast agent are administered to the patient as a single composition. In some embodiments, the single composition further comprises an aqueous solvent. In some embodiments, the T1-reducing contrast agent and the T2-reducing contrast agent are administered to the patient as two separate compositions; wherein a first composition comprises the T1-reducing contrast agent and a second composition comprises the T2-reducing agent. In some embodiments, the two separate compositions each further comprise an aqueous solvent. In some embodiments, administering T1-reducing contrast agent and the T2-reducing contrast agent are completed simultaneously. In some embodiments, imaging the patient comprises imaging via magnetic resonance imaging. In some embodiments, imaging the patient is performed within about 10 minutes of administration of the T1-reducing contrast agent and the T2-reducing contrast agent.

In some embodiments, the first T1-reducing contrast agent comprises a gadolinium compound. In some embodiments, the gadolinium compound is selected from gadopentetate dimeglumine (Gd-DTPA), gadoterate meglumine, gadoversetamide, gadoteridol, gadodiamide, gadobenate dimeglumine, gadobutrol, gadoxetate disodium, gadofosveset trisodium and combinations thereof. In some embodiments, the gadolinium compound is encapsulated in liposomes.

In some embodiments, the T2-reducing contrast agent comprises an iron oxide. In some embodiments, the iron oxide is selected from iron (II) oxide, iron (III) oxide, ferumoxytol (Feraheme), Feraspin XS, Feraspin S, Feraspin M, Feraspin R, Feraspin L, Feraspin XL, iron nickel oxide nanopowder, iron oxide (II,III) magnetic nanoparticles, iron-nickel alloy nanopowder, magnetic iron oxide nanoparticles, carbon coated iron nanopowder, and combinations thereof. In some embodiments, the iron oxide is encapsulated in liposomes.

In some embodiments, administration of the T1-reducing contrast agent and the T2-reducing contrast agent is achieved by administration to the patient's cardiovascular system.

Some embodiments are directed to methods for detecting ischemic endocardium in a patient comprising: administering a T1-reducing contrast agent and a T2-reducing contrast agent to the patient; and imaging the patient's heart; wherein diffusion of the T1 reducing contrast agent across the endocardium is indicative of ischemic endocardium.

In some embodiments, the particle size of the T2-reducing contrast agent is larger than the particle size of the T1-reducing contrast agent. In some embodiments, the T1-reducing agent, the T2-reducing agent, or a combination thereof further comprises an aqueous solvent. In some embodiments, the T1-reducing contrast agent and the T2-reducing contrast agent are administered to the patient as a single composition; wherein the single composition comprises the T1-reducing contrast agent and the T2-reducing contrast agent. In some embodiments, the single composition further comprises an aqueous solvent. In some embodiments, the T1-reducing agent and the T2-reducing contrast agent are administered to the patient as two separate compositions; wherein a first composition comprises the T1-reducing .contrast agent; and wherein a second composition comprises the T2-reducing contrast agent. In some embodiments, the two separate compositions each further comprise an aqueous solvent. In some embodiments, administering T1-reducing contrast agent and the T2-reducing contrast agent are completed simultaneously.

In some embodiments, imaging the patient's heart comprises imaging via magnetic resonance imaging. In some embodiments, imaging the patient's heart is performed within about 10 minutes of administration of the T1-reducing contrast agent and the T2-reducing contrast agent.

In some embodiments, the first T1-reducing contrast agent comprises a gadolinium compound. In some embodiments, the gadolinium compound is selected from gadopentetate dimeglumine (Gd-DTPA), gadoterate meglumine, gadoversetamide, gadoteridol, gadodiamide, gadobenate dimeglumine, gadobutrol, gadoxetate disodium, gadofosveset trisodium and combinations thereof. In some embodiments, the gadolinium compound is encapsulated in liposomes.

In some embodiments, the T2-reducing contrast agent comprises an iron oxide. In some embodiments, the iron oxide is selected from iron (II) oxide, iron (III) oxide, ferumoxytol (Feraheme), Feraspin XS, Feraspin S, Feraspin M, Feraspin R, Feraspin L, Feraspin XL, iron nickel oxide nanopowder, iron oxide (II,III) magnetic nanoparticles, iron-nickel alloy nanopowder, magnetic iron oxide nanoparticles, carbon coated iron nanopowder, and combinations thereof. In some embodiments, the iron oxide is encapsulated in liposomes.

In some embodiments, administration of the T1-reducing contrast agent and the T2-reducing contrast agent is achieved by administration to the patient's cardiovascular system.

Some embodiments are directed to methods for detecting ischemic endocardium in a patient comprising: imaging the patient after administering a T1-reducing contrast agent and a T2-reducing contrast agent to the patient; wherein diffusion of the T1 reducing contrast agent across the endocardium is indicative of ischemic endocardium.

In some embodiments, the particle size of the T2-reducing contrast agent is larger than the particle size of the T1-reducing contrast agent. In some embodiments, the T1-reducing agent, the T2-reducing agent, or a combination thereof further comprises an aqueous solvent. In some embodiments, the T1-reducing contrast agent and the T2-reducing contrast agent are administered to the patient as a single composition. In some embodiments, the single composition further comprises an aqueous solvent. In some embodiments, the T1-reducing contrast agent and the T2-reducing contrast agent are administered to the patient as two separate compositions; wherein a first composition comprises the T1-reducing contrast agent and a second composition comprises the T2-reducing agent. In some embodiments, the two separate compositions each further comprise an aqueous solvent. In some embodiments, administering T1-reducing contrast agent and the T2-reducing contrast agent are completed simultaneously.

In some embodiments, imaging the patient comprises imaging via magnetic resonance imaging. In some embodiments, imaging the patient is performed within about 10 minutes of administration of the T1-reducing contrast agent and the T2-reducing contrast agent.

In some embodiments, the first T1-reducing contrast agent comprises a gadolinium compound. In some embodiments, the gadolinium compound is selected from gadopentetate dimeglumine (Gd-DTPA), gadoterate meglumine, gadoversetamide, gadoteridol, gadodiamide, gadobenate dimeglumine, gadobutrol, gadoxetate disodium, gadofosveset trisodium and combinations thereof. In some embodiments, the gadolinium compound is encapsulated in liposomes.

In some embodiments, the T2-reducing contrast agent comprises an iron oxide. In some embodiments, the iron oxide is selected from iron (II) oxide, iron (III) oxide, ferumoxytol (Feraheme), Feraspin XS, Feraspin S, Feraspin M, Feraspin R, Feraspin L, Feraspin XL, iron nickel oxide nanopowder, iron oxide (II,III) magnetic nanoparticles, iron-nickel alloy nanopowder, magnetic iron oxide nanoparticles, carbon coated iron nanopowder, and combinations thereof. In some embodiments, the iron oxide is encapsulated in liposomes.

In some embodiments, administration of the T1-reducing contrast agent and the T2-reducing contrast agent is achieved by administration to the patient's cardiovascular system.

BRIEF DESCRIPTION OF THE FIGURES

FIG. 1A is an MRI image of an MRI bladder phantom model system. FIG. 1A is an impermeable MRI bladder phantom with no T1-reducing contrast agent diffusion.

FIG. 1B is an MRI image of an MRI bladder phantom model system. FIG. 1B is a permeable MRI bladder phantom with T1-reducing contrast agent diffusion into the surrounding tissue.

FIG. 2 is an image of an MRI bladder phantom.

DETAILED DESCRIPTION

Figure 3:
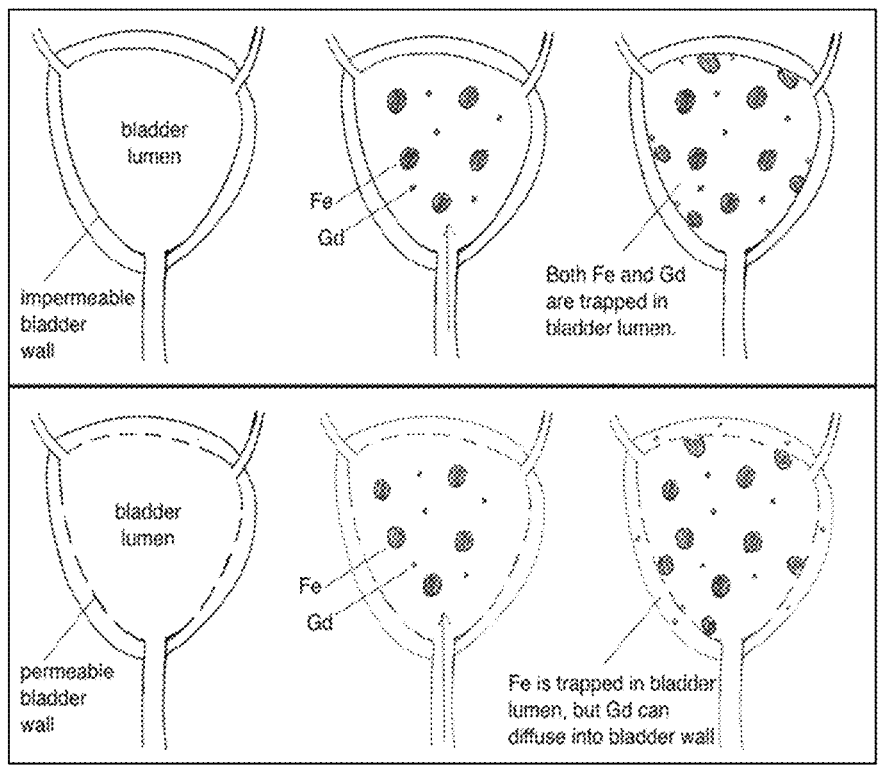
FIG. 3 is a schematic displaying the principle of administering a T1-reducing contrast agent and a T2-reducing contrast agent to the bladder to measure permeability.

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

Optical Isomers, Diastereomers, Geometric Isomers, and Tautomers. Compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. The formulas are shown without a definitive stereochemistry at certain positions. The present invention includes all stereoisomers of such formulas and pharmaceutically acceptable salts thereof. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general formula may be obtained by stereospecific synthesis using optically pure starting materials or reagents of known configuration.

It must also be noted that as used herein and in the appended claims, the singular forms "a", "an", and "the" include plural reference unless the context clearly dictates otherwise. Thus, for example, reference to a "fibroblast" is a reference to one or more fibroblasts and equivalents thereof known to those skilled in the art, and so forth.

As used herein, the term "about" means plus or minus 10% of the numerical value of the number with which it is being used. Therefore, about 50% means in the range of 45%-55%.

"Administering" when used in conjunction with the imaging compositions containing the T1-reducing contrast agents, T2-reducing contrast agents, or combinations thereof, described herein means to administer the agent, agents or compositions directly into, or onto a target body cavity or to administer the agent, agents or compositions to a patient whereby the agent or agents impacts the body cavity to which it is targeted. Thus, as used herein, the term "administering", when used in conjunction with any agent, agents, or compositions described herein, can include, but is not limited to, providing an agent, agents, or compositions into or onto the target body cavity; providing an agent, agents, or composition systemically to a patient by, e.g., intravenous injection whereby the agent or agents reaches the target tissue; administering the agent, agents or compositions described herein to the lumen of a body cavity. "Administering" a composition may be accomplished by injection, instillation, catheterization, or by either method in combination with other known techniques. "Administering" agent, agents or compositions described herein to the lumen of a body cavity can also be achieved through a natural opening to the body cavity. For example, the agent, agents or compositions described herein can be administered to the lumen of the urinary bladder via the urethra. In some embodiments, the agent, agents or compositions described herein are administered to the body cavity via instillation. For example, in some embodiments, the agent, agents or compositions described herein are administered to the urinary bladder via instillation with a urinary catheter. In another example, the agent, agents or compositions described herein can be administered to the lumen of a blood vessel via intravenous injection. In yet another example the agent, agents or compositions described herein can be administered to the lumen of the gastrointestinal tract via oral administration.

The term "animal" as used herein includes, but is not limited to, humans and non-human vertebrates such as wild, domestic and farm animals.

By "pharmaceutically acceptable", it is meant the carrier, diluent or excipient must be compatible with the other ingredients of the formulation and not deleterious to the recipient thereof.

The term "liposome" generally refers to spherical or roughly spherical particles containing an internal cavity. The walls of liposomes can include a bilayer of lipids. These lipids can be phospholipids. Numerous lipids and/or phospholipids may be used to make liposomes. One example are amphipathic lipids having hydrophobic and polar head group moieties which may form spontaneously into bilayer vesicles in water, as exemplified by phospholipids, or which may be stably incorporated into lipid bilayers, with their hydrophobic moiety in contact with the interior, hydrophobic region of the bilayer membrane, and their polar head group moiety oriented toward the exterior, polar surface of the membrane.

The term "body cavity" refers to any fluid filled space in a multicellular organism including but not limited the cardiovascular system, the heart, blood vessels, lymph vessels, coelom, pericardial cavity, pericardium, intraembryonic coelom, extraembryonic coelom, chorionic cavity, dorsal cavity, ventral cavity, thoracic cavity, abdominopelvic cavity, cranial cavity, spinal cavity (or vertebral cavity), a pleural cavity, superior mediastinum, thoracic cavity, abdominal cavity, pelvic cavity, abdominopelvic cavity, urinary bladder, kidneys, ureters, gastrointestinal tract, stomach, intestines, liver, gallbladder, pancreas, anus, reproductive system or any combination thereof. In some embodiments, the body cavity is naturally fluid filled. In some embodiments, the body cavity is artificially fluid filled.

The term "cardiovascular system" refers to a closed organ system made up of the heart and blood vessels (including arteries, veins and capillaries, coronary vessels, portal veins) of a vertebrate organism such as a mammal, and more preferably a human.

The term "gastrointestinal tract" refers to a an organ system made up of the stomach and intestines (including the small and large intestines, appendix) of a vertebrate organism such as a mammal, and more preferably a human. The gastrointestinal tract may also include all structures between the mouth and the anus (including the esophagus, stomach, small and large intestines, appendix, and rectum) of a vertebrate organism such as a mammal, and more preferably a human.

As used herein, the term "lumen" refers to the interior space of a body cavity. In some embodiment, the lumen of a body cavity is enclosed by a luminal wall, the porosity of which can be measured using the methods and compositions described herein.

As used herein, the term "contrast agent" refers to a compound or molecule that can be used in the imaging of body cavity and which affects and/or enhances the contrast of structures and/or fluids in the body. In some embodiments, the term "contrast agent" refers to a paramagnetic and/or superparamagnetic compound or molecule that can be used in the imaging of body cavity. In some embodiments, a particular contrast agent may have a T1-reducing contrast effect (spin-spin relaxation), a T2-contrast reducing effect (spin-lattice relaxation) or a combination thereof. As used herein, one or more contrast agents may be incorporated into a composition which may then be administered to a patient to image a body cavity.

The present disclosure generally relates to systems and methods for providing a diagnostic examination to a patient, including, but not limited to a determination of the permeability of a patients' body cavity. In some embodiments, such diagnostic examination may generally include measurement of patency and/or porosity of the body cavity by observing the diffusion of a non-invasively detectable molecular agent across the luminal surface of the body cavity. In some embodiments, such diagnostic examination may generally include measurement of permeability, patency and/or porosity of the body cavity by observing the diffusion of a non-invasively detectable molecular agent out the lumen of the body cavity. In some embodiments, the systems and methods described herein may be used for determining altered permeability of the lining of other body cavities, such as, for example, cardiovascular system, blood vessels, the heart, the vagina, gut, sinus and oral cavities or a combination thereof. Some embodiments are directed to a method for measuring the permeability of a body cavity in a patient.

In some embodiments, present disclosure generally relates to systems and methods for providing a diagnostic examination to a patient, including, but not limited to detection of patent foramen ovale (PFO). In some embodiments, such diagnostic examination may generally include measurement of patency and/or porosity of the body cavity by observing the diffusion of a non-invasively detectable molecular agent across the luminal surface of the body cavity. In some embodiments, such diagnostic examination may generally include measurement of patency and/or porosity of the body cavity by observing the diffusion of a non-invasively detectable molecular agent out the lumen of the body cavity. In some embodiments, the systems and methods described herein may also be used for determining altered permeability of the lining of other body cavities, such as, for example, the vagina, gut, sinus and oral cavities. Some embodiments are directed to a diagnostic examination of a patient's heart. In particular embodiments, such diagnostic examination may generally include detection of PFO, ischemic endocardium or a combination thereof. In some embodiments, the systems and methods described herein may be used for diagnosing PFO. In some embodiments, the systems and methods described herein may be used for diagnosing ischemic endocardium.

The present disclosure generally relates to systems and methods for providing a diagnostic examination to a patient, including, but not limited to a determination of the permeability of a patients' body cavity. In some embodiments, such diagnostic examination may generally include measurement of patency and/or porosity of the body cavity by observing the diffusion of a non-invasively detectable molecular agent across the luminal surface of the body cavity. In some embodiments, such diagnostic examination may generally include measurement of patency and/or porosity of the body cavity by observing the diffusion of a non-invasively detectable molecular agent out the lumen of the body cavity. In some embodiments, the systems and methods described herein may be used for determining altered permeability of the lining of other body cavities, such as, for example, the vagina, gut, sinus and oral cavities. Some embodiments are directed to a diagnostic examination of a patient's urinary bladder. In particular embodiments, such diagnostic examination may generally include measurement of urothelial patency and/or porosity by observing the diffusion of a non-invasively detectable molecular agent across the urothelium of the urinary bladder. In some embodiments, the systems and methods described herein may be used for diagnosing other bladder conditions that have altered barrier permeability, such as, for example, radiation cystitis, hemorrhagic cystitis, bladder cancer and bladder infection Some embodiments are directed to a method for measuring the permeability of a body cavity in a patient.

The methods and contrast agents described herein may also be utilized in the detection and diagnosis of diseases caused by, or associated with, pathologic breakdown of the inner layers of arterial walls, such as, but not limited to: post-embolic or pre-hemorrhagic stroke breakdown of the blood-brain-barrier (BBB), vasculitis, ruptured atherosclerotic plaque, diabetic vasculopathy, inflammation, vasculitis, autoimmune diseases, infection, cancer, septic shock, or a combination thereof.

PFO is characterized by a hole located in the septum of the heart between the right and left atria, typically about 1 mm in size. PFO is a known cause of embolic stroke where small blood clots may bypass the filter of the lung capillary bed and become ejected out the heart into the aorta and through the systemic and cerebral circulation. The PFO works like a flap valve, only opening during certain conditions when there is more pressure inside the chest. This increased pressure occurs when a subjects strain while having, for example, a bowel movement, cough, or sneeze. If the resulting pressure is great enough, blood may travel from the right atrium to the left atrium. If there is a clot or particles in the blood traveling in the right side of the heart, it can cross the PFO, enter the left atrium, and travel out of the heart and to the brain (causing a stroke) or into a coronary artery (causing a heart attack).

Embodiments herein are directed to methods for detecting PFO in a patient comprising: administering a T1-reducing contrast agent and a T2-reducing contrast agent to the patient; and imaging the patient's heart; wherein diffusion of the T2 reducing contrast agent into the left heart is indicative of PFO.

In some embodiments, the T1 reducing agent is able to pass freely through the circulatory system and enter the left heart cavity, whereas the T2 reducing agent is filtered by the lung capillaries such that in a subject without PFO, only the T1 reducing agent is able to enter the left heart cavity. Conversely, in a subject with PFO, the T2 reducing agent will be able to enter the left heart cavity via the hole(s) in the heart between the right and left atria. The result is that, in a healthy subject, only the T1 reducing agent will be present in the left heart whereas with a subject with PFO both the T1 reducing agent and T2 reducing agent will be present in the left heart.

Some embodiments are directed to methods for detecting PFO in a patient comprising: imaging the patient's heart after administering a T1-reducing contrast agent and a T2-reducing contrast agent to the patient; wherein diffusion of the T2 reducing contrast agent from the right atrium to the left atrium is indicative of PFO. In some embodiments, diffusion of the T2 reducing contrast agent from the right atrium to the left atrium is indicative of PFO. In some embodiments, the absence of the PFO prevents the T2 reducing contrast agent from diffusing from the right atrium to the left atrium. In some embodiments, the T1 reducing contrast agent is able to circulate freely through the vasculature due to its small size. In some embodiments, the particle size of the T2-reducing contrast agent is larger than the particle size of the T1-reducing contrast agent. In some embodiments, the average particle size of the T2-reducing contrast agent is larger than the average particle size of the T1-reducing contrast agent. In some embodiments, the particle size of the majority of the particles comprising the T2-reducing contrast agent is larger than the particle size of the majority of the particles comprising the T1-reducing contrast agent. In some embodiments, the particle size of about 90% to about 99% of the particles comprising the T2-reducing contrast agent is larger than the particle size of about 90% to about 99% of the particles comprising the T1-reducing contrast agent. In some embodiments, the particle size of about 90% of the particles comprising the T2-reducing contrast agent is larger than the particle size of about 90% of the particles comprising the T1-reducing contrast agent. In some embodiments, the particle size of about 95% of the particles comprising the T2-reducing contrast agent is larger than the particle size of about 95% of the particles comprising the T1-reducing contrast agent. In some embodiments, the particle size of about 99% of the particles comprising the T2-reducing contrast agent is larger than the particle size of about 99% of the particles comprising the T1-reducing contrast agent.

Some embodiments are directed to the use of imaging compositions comprising a T1-reducing contrast agent and T2-reducing contrast agent, which may be administered to cardiovascular system of a subject, where each of the contrast agents have different size particles and have different contrast effects. For example, relatively large iron oxide particles (having approximate diameters from about 3.5 and about 80 microns) will reduce local T2 (spin-spin relaxation) times, and relatively small gadolinium chelate particles (having approximate diameters from about 7 to about 11 angstroms) will reduce local T1 (spin-lattice relaxation) times. Without wishing to be bound by theory, the use of particles with differing particle size and contrast effect results in a differential distribution in the subjects' cardiovascular system due to filtration by lung capillaries that prevent larger particles from entering the right side of the heart and to the rest of the body via the systemic arteries. In a subject without PFO, the smaller particles (i.e. gadolinium particles) can diffuse throughout the cardiovascular system, whereas the larger particles (i.e. iron oxide particles) are restricted to the right side of the heart and pulmonary arteries and are prevented from diffusing past the lungs due to their larger size. In yet other embodiments, in a permeable body cavity, the smaller particles (i.e. gadolinium particles) can diffuse out of the lumen of the body cavity into the luminal wall and surrounding tissue, whereas the larger particles (i.e. iron oxide particles) remain in the lumen. Because iron and gadolinium have opposite effects on magnetic resonance imaging signal intensity, once the smaller particles have diffused across the luminal surface of the body cavity, or out of the lumen of the body cavity, they can now be visualized without interference or masking by the contrast effect of the larger particles. For example, iron oxide particles reduce image signal intensity within their immediate vicinity, whereas the gadolinium particles increase signal intensity within their immediate vicinity and the result of both particles being present in the lumen of a body cavity is an overall decrease in signal intensity masking the contrast effect of the gadolinium particle. Therefore, when the lumen of a body cavity is intact and impermeable, the contrast effect of the smaller gadolinium particle is masked by the contrast effect of the larger iron particles.

In some embodiments, the relative concentrations of the T1-reducing contrast agent and T2-reducing contrast agent used may be optimized so that the concentration of the T2-reducing contrast agent (i.e. iron oxide particles) is strong enough to completely mask the effect of the T1-reducing contrast agent (i.e. gadolinium) within the lumen of a blood vessel. Thus, when the blood vessel is impermeable, there is virtually no signal, or image intensity, present within the lumen of the blood vessel. However, when administered to a permeable blood vessel, the T1-reducing contrast agent, (i.e. gadolinium chelate) is able to diffuse across the luminal surface of the blood vessel, or out of the lumen of the blood vessel, and escape the vicinity of the T2-reducing contrast agent (i.e. iron oxide particles), which are too large to diffuse across the luminal surface of the blood vessel, or out of the lumen of the blood vessel. In some embodiments, the result is that the wall of a permeable blood vessel will appear as a bright ring on an MRI image, including a slice selective MRI image that includes the blood vessel and surrounding tissue, whereas in the case of an impermeable blood vessel, the wall of said blood vessel will not be visible on an MRI image, including a slice selective MRI image that includes the blood vessel and surrounding tissue. In other embodiments, in the case of an impermeable blood vessel, the wall of said blood vessel will be visible on an MRI image, including a slice selective MRI image that includes the blood vessel and surrounding tissue, but will not have the bright ring enhancement of the T1-reducing contrast agent.

In some embodiments, the methods of detecting PFO described herein may additionally, or alternatively, be utilized to measure the permeability of the luminal lining of a body cavity, the permeability of the luminal surface of a body cavity or a combination thereof. In some embodiments, detecting PFO described herein may include measuring the permeability of the luminal lining of a body cavity, the permeability of the luminal surface of a body cavity or a combination thereof.

Embodiments herein are directed to methods for detecting ischemic endocardium in a patient comprising: administering a T1-reducing contrast agent and a T2-reducing contrast agent to the patient; and imaging the patient's heart; wherein diffusion of the T1 reducing contrast agent into the left heart is indicative of ischemic endocardium.

The endocardium is the thin inner cellular lining of the heart cavities, including the left ventricle. Sufficient ischemia to a segment of the left ventricle results in a breakdown of the cells and cell-cell junctions in the endocardium.

In some embodiments, ischemic endocardium can be detected by measurement of the permeability of the endocardium in a patient comprising: administering a T1-reducing contrast agent and a T2-reducing contrast agent to the patient; and imaging the patient's heart; wherein diffusion of the T1 reducing contrast agent across the luminal surface of the endocardium is indicative of permeability, which in turn may be indicative of ischemic endocardium. In some embodiments, diffusion of the T1 reducing contrast agent out of the lumen of the endocardium is indicative of permeability, which in turn may be indicative of ischemic endocardium.

Some embodiments are directed to methods for detecting ischemic endocardium in a patient comprising: imaging the patient's heart after administering a T1-reducing contrast agent and a T2-reducing contrast agent to the patient; wherein diffusion of the T1 reducing contrast agent across the luminal surface of the endocardium is indicative of permeability, which in turn may be indicative of ischemic endocardium. In some diffusion of the T1 reducing contrast agent out of the lumen of the endocardium is indicative of permeability, which in turn may be indicative of ischemic endocardium. In some embodiments, the particle size of the T2-reducing contrast agent is larger than the particle size of the T1-reducing contrast agent. In some embodiments, the average particle size of the T2-reducing contrast agent is larger than the average particle size of the T1-reducing contrast agent. In some embodiments, the particle size of the majority of the particles comprising the T2-reducing contrast agent is larger than the particle size of the majority of the particles comprising the T1-reducing contrast agent. In some embodiments, the particle size of about 90% to about 99% of the particles comprising the T2-reducing contrast agent is larger than the particle size of about 90% to about 99% of the particles comprising the T1-reducing contrast agent. In some embodiments, the particle size of about 90% of the particles comprising the T2-reducing contrast agent is larger than the particle size of about 90% of the particles comprising the T1-reducing contrast agent. In some embodiments, the particle size of about 95% of the particles comprising the T2-reducing contrast agent is larger than the particle size of about 95% of the particles comprising the T1-reducing contrast agent. In some embodiments, the particle size of about 99% of the particles comprising the T2-reducing contrast agent is larger than the particle size of about 99% of the particles comprising the T1-reducing contrast agent.

Some embodiments are directed to the use of imaging compositions comprising a T1-reducing contrast agent and T2-reducing contrast agent, which may be administered to the lumen of a body cavity for detecting ischemic endocardium, where each of the contrast agents have different size particles and have different contrast effects. For example, relatively large iron oxide particles (having approximate diameters from about 3.5 and about 80 microns) will reduce local T2 (spin-spin relaxation) times, and relatively small gadolinium chelate particles (having approximate diameters from about 7 to about 11 angstroms) will reduce local T1 (spin-lattice relaxation) times. Without wishing to be bound by theory, the use of particles with differing particle size and contrast effect results in a differential distribution in lumen and luminal wall of the endocardium depending on whether the endocardium is permeable. In a permeable body cavity, the smaller particles (i.e. gadolinium particles) can diffuse across the luminal surface of the endocardium into the luminal wall and surrounding tissue, whereas the larger particles (i.e. iron oxide particles) remain in the lumen. In yet other embodiments, in a permeable endocardium, the smaller particles (i.e. gadolinium particles) can diffuse out of the lumen of the endocardium into the luminal wall and surrounding tissue, whereas the larger particles (i.e. iron oxide particles) remain in the lumen. Because iron and gadolinium have opposite effects on magnetic resonance imaging signal intensity, once the smaller particles have diffused across the luminal surface of the endocardium, or out of the lumen of the endocardium, they can now be visualized without interference or masking by the contrast effect of the larger particles. For example, iron oxide particles reduce image signal intensity within their immediate vicinity, whereas the gadolinium particles increase signal intensity within their immediate vicinity and the result of both particles being present in the lumen of the endocardium is an overall decrease in signal intensity masking the contrast effect of the gadolinium particle. Therefore, when the lumen of the endocardium is intact and impermeable, the contrast effect of the smaller gadolinium particle is masked by the contrast effect of the larger iron particles.

In some embodiments, the relative concentrations of the T1-reducing contrast agent and T2-reducing contrast agent used may be optimized so that the concentration of the T2-reducing contrast agent (i.e. iron oxide particles) is strong enough to completely mask the effect of the T1-reducing contrast agent (i.e. gadolinium) within the lumen of the endocardium. Thus, when the endocardium is impermeable, there is virtually no signal, or image intensity, present within the lumen of the endocardium. However, when administered to a permeable endocardium, the T1-reducing contrast agent, (i.e. gadolinium chelate) is able to diffuse across the luminal surface of the endocardium, or out of the lumen of the endocardium, and escape the vicinity of the T2-reducing contrast agent (i.e. iron oxide particles), which are too large to diffuse across the luminal surface of the endocardium, or out of the lumen of the endocardium. In some embodiments, the result is that the wall of a permeable endocardium will appear as a bright ring on an MRI image, including a slice selective MRI image that includes the endocardium and surrounding tissue, whereas in the case of an impermeable endocardium, the wall of said endocardium will not be visible on an MRI image, including a slice selective MRI image that includes the endocardium and surrounding tissue. In other embodiments, in the case of an impermeable endocardium, the wall of said endocardium will be visible on an MRI image, including a slice selective MRI image that includes the endocardium and surrounding tissue, but will not have the bright ring enhancement of the T1-reducing contrast agent.

Embodiments herein are directed to methods for detecting a condition associated with the pathological breakdown of the layers of epithelial cells and cell junctions that line the gastrointestinal tract in a patient comprising: administering a T1-reducing contrast agent and a T2-reducing contrast agent to the patient; and imaging the patient's gastrointestinal tract; wherein diffusion of the T1 reducing contrast agent into the left heart is indicative of a condition associated with the pathological breakdown of the layers of epithelial cells and cell junctions that line the gastrointestinal tract. In some embodiments, the T1-reducing contrast agent and the T1-reducing contrast agent are administered orally. In some embodiments, conditions associated with the pathological breakdown of the layers of epithelial cells and cell junctions that line the gastrointestinal tract include but are not limited to inflammatory bowel disease, gastric/duodenal ulcer disease, celiac disease, or any combination thereof.

In some embodiments, a condition associated with the pathological breakdown of the layers of epithelial cells and cell junctions that line the gastrointestinal tract can be detected by measurement of the permeability of the gastrointestinal tract lumen in a patient comprising: administering a T1-reducing contrast agent and a T2-reducing contrast agent to the patient; and imaging the patient's gastrointestinal tract; wherein diffusion of the T1 reducing contrast agent across the luminal surface of the gastrointestinal tract is indicative of permeability, which in turn may be indicative of a condition associated with the pathological breakdown of the layers of epithelial cells and cell-junctions that line the gastrointestinal tract. In some embodiments, diffusion of the T1 reducing contrast agent out of the lumen of the gastrointestinal tract is indicative of permeability, which in turn may be indicative of a condition associated with the pathological breakdown of the layers of epithelial cells and cell junctions that line the gastrointestinal tract. In some embodiments, the T1-reducing contrast agent and the T1-reducing contrast agent are administered orally. In some embodiments conditions associated with the pathological breakdown of the layers of epithelial cells and cell-junctions that line the gastrointestinal tract include but are not limited to inflammatory bowel disease, gastric/duodenal ulcer disease, celiac disease or combinations thereof.

Some embodiments are directed to methods for detecting a condition associated with the pathological breakdown of the layers of epithelial cells and cell junctions that line the gastrointestinal tract in a patient comprising: imaging the patient's gastrointestinal tract after administering a T1-reducing contrast agent and a T2-reducing contrast agent to the patient; wherein diffusion of the T1 reducing contrast agent across the luminal surface of the gastrointestinal tract is indicative of permeability, which in turn may be indicative of a condition associated with the pathological breakdown of the layers of epithelial cells and cell junctions that line the gastrointestinal tract. In some diffusion of the T1 reducing contrast agent out of the lumen of the gastrointestinal tract is indicative of permeability, which in turn may be indicative of a condition associated with the pathological breakdown of the layers of epithelial cells and cell junctions that line the gastrointestinal tract. In some embodiments, the particle size of the T2-reducing contrast agent is larger than the particle size of the T1-reducing contrast agent. In some embodiments, the average particle size of the T2-reducing contrast agent is larger than the average particle size of the T1-reducing contrast agent. In some embodiments, the particle size of the majority of the particles comprising the T2-reducing contrast agent is larger than the particle size of the majority of the particles comprising the T1-reducing contrast agent. In some embodiments, the particle size of about 90% to about 99% of the particles comprising the T2-reducing contrast agent is larger than the particle size of about 90% to about 99% of the particles comprising the T1-reducing contrast agent. In some embodiments, the particle size of about 90% of the particles comprising the T2-reducing contrast agent is larger than the particle size of about 90% of the particles comprising the T1-reducing contrast agent. In some embodiments, the particle size of about 95% of the particles comprising the T2-reducing contrast agent is larger than the particle size of about 95% of the particles comprising the T1-reducing contrast agent. In some embodiments, the particle size of about 99% of the particles comprising the T2-reducing contrast agent is larger than the particle size of about 99% of the particles comprising the T1-reducing contrast agent. In some embodiments, the T1-reducing contrast agent and the T2-reducing contrast agent are administered orally. In some embodiments conditions associated with the pathological breakdown of the layers of epithelial cells and cell junctions that line the gastrointestinal tract include but are not limited to inflammatory bowel disease, gastric/duodenal ulcer disease, celiac disease, or combinations thereof.

Some embodiments are directed to the use of imaging compositions comprising a T1-reducing contrast agent and T2-reducing contrast agent, which may be administered to the lumen of a body cavity for detecting a condition associated with the pathological breakdown of the layers of epithelial cells and cell junctions that line the gastrointestinal tract, where each of the contrast agents have different size particles and have different contrast effects. For example, relatively large iron oxide particles (having approximate diameters from about 3.5 and about 80 microns) will reduce local T2 (spin-spin relaxation) times, and relatively small gadolinium chelate particles (having approximate diameters from about 7 to about 11 angstroms) will reduce local T1 (spin-lattice relaxation) times. Without wishing to be bound by theory, the use of particles with differing particle size and contrast effect results in a differential distribution in lumen and luminal wall of the gastrointestinal tract depending on whether the lumen is permeable. In a permeable body cavity, the smaller particles (i.e. gadolinium particles) can diffuse across the luminal surface of the gastrointestinal tract into the luminal wall and surrounding tissue, whereas the larger particles (i.e. iron oxide particles) remain in the lumen. In yet other embodiments, in a permeable gastrointestinal tract, the smaller particles (i.e. gadolinium particles) can diffuse out of the lumen of the gastrointestinal tract into the luminal wall and surrounding tissue, whereas the larger particles (i.e. iron oxide particles) remain in the lumen. Because iron and gadolinium have opposite effects on magnetic resonance imaging signal intensity, once the smaller particles have diffused across the luminal surface of the gastrointestinal tract, or out of the lumen of the endocardium, they can now be visualized without interference or masking by the contrast effect of the larger particles. For example, iron oxide particles reduce image signal intensity within their immediate vicinity, whereas the gadolinium particles increase signal intensity within their immediate vicinity and the result of both particles being present in the lumen of the gastrointestinal tract is an overall decrease in signal intensity masking the contrast effect of the gadolinium particle. Therefore, when the lumen of the gastrointestinal tract is intact and impermeable, the contrast effect of the smaller gadolinium particle is masked by the contrast effect of the larger iron particles. In some embodiments, the compositions comprising a T1-reducing contrast agent and T2-reducing contrast agent are administered orally. In some embodiments condition associated with the pathological breakdown of the layers of epithelial cells and cell junctions that line the gastrointestinal tract include but are not limited to inflammatory bowel disease, gastric/duodenal ulcer disease, celiac disease, or combinations thereof.

In some embodiments, the relative concentrations of the T1-reducing contrast agent and T2-reducing contrast agent used may be optimized so that the concentration of the T2-reducing contrast agent (i.e. iron oxide particles) is strong enough to completely mask the effect of the T1-reducing contrast agent (i.e. gadolinium) within the lumen of the gastrointestinal tract. Thus, when the endocardium is impermeable, there is virtually no signal, or image intensity, present within the lumen of the gastrointestinal tract. However, when administered to a permeable gastrointestinal tract, the T1-reducing contrast agent, (i.e. gadolinium chelate) is able to diffuse across the luminal surface of the gastrointestinal tract, or out of the lumen of the gastrointestinal tract, and escape the vicinity of the T2-reducing contrast agent (i.e. iron oxide particles), which are too large to diffuse across the luminal surface of the gastrointestinal tract, or out of the lumen of the gastrointestinal tract. In some embodiments, the result is that the wall of a permeable gastrointestinal tract will appear as a bright ring on an MRI image, including a slice selective MRI image that includes the gastrointestinal tract and surrounding tissue, whereas in the case of an impermeable gastrointestinal tract, the wall of said endocardium will not be visible on an MRI image, including a slice selective MRI image that includes the gastrointestinal tract and surrounding tissue. In other embodiments, in the case of an impermeable gastrointestinal tract, the wall of said gastrointestinal tract will be visible on an MRI image, including a slice selective MRI image that includes the gastrointestinal tract and surrounding tissue, but will not have the bright ring enhancement of the T1-reducing contrast agent.

Embodiments herein are directed to methods for measuring the permeability of a body cavity in a patient comprising: administering a T1-reducing contrast agent and a T1-reducing contrast agent to the patient; and imaging the patient; wherein diffusion of the T1 reducing contrast agent across the luminal surface of the body cavity is indicative of permeability. In some embodiments, diffusion of the T1 reducing contrast agent out of the lumen of the body cavity is indicative of permeability.

In some embodiments, the methods of measuring the permeability of a body cavity described herein may additionally, or alternatively, be utilized to measure the permeability of the luminal lining of a body cavity, the permeability of the luminal surface of a body cavity or a combination thereof. In some embodiments, measuring the permeability of a body cavity described herein may include measuring the permeability of the luminal lining of a body cavity, the permeability of the luminal surface of a body cavity or a combination thereof.

Some embodiments are directed to methods for measuring the permeability of a body cavity in a patient comprising: imaging the patient after administering a T1-reducing contrast agent and a T2-reducing contrast agent to the patient; wherein diffusion of the T1 reducing contrast agent across the luminal surface of the body cavity is indicative of permeability. In some diffusion of the T1 reducing contrast agent out of the lumen of the body cavity is indicative of permeability. In some embodiments, the particle size of the T2-reducing contrast agent is larger than the particle size of the T1-reducing contrast agent. In some embodiments, the average particle size of the T2-reducing contrast agent is larger than the average particle size of the T1-reducing contrast agent. In some embodiments, the particle size of the majority of the particles comprising the T2-reducing contrast agent is larger than the particle size of the majority of the particles comprising the T1-reducing contrast agent. In some embodiments, the particle size of about 90% to about 99% of the particles comprising the T2-reducing contrast agent is larger than the particle size of about 90% to about 99% of the particles comprising the T1-reducing contrast agent. In some embodiments, the particle size of about 90% of the particles comprising the T2-reducing contrast agent is larger than the particle size of about 90% of the particles comprising the T1-reducing contrast agent. In some embodiments, the particle size of about 95% of the particles comprising the T2-reducing contrast agent is larger than the particle size of about 95% of the particles comprising the T1-reducing contrast agent. In some embodiments, the particle size of about 99% of the particles comprising the T2-reducing contrast agent is larger than the particle size of about 99% of the particles comprising the T1-reducing contrast agent.

Some embodiments are directed to the use of imaging compositions comprising a T1-reducing contrast agent and T2-reducing contrast agent, which may be administered to the lumen of a body cavity, where each of the contrast agents have different size particles and have different contrast effects. For example, relatively large iron oxide particles (having approximate diameters from about 3.5 and about 80 microns) will reduce local T2 (spin-spin relaxation) times, and relatively small gadolinium chelate particles (having approximate diameters from about 7 to about 11 angstroms) will reduce local T1 (spin-lattice relaxation) times. Without wishing to be bound by theory, the use of particles with differing particle size and contrast effect results in a differential distribution in lumen and luminal wall of a body cavity depending on whether the body cavity is permeable. In a permeable body cavity, the smaller particles (i.e. gadolinium particles) can diffuse across the luminal surface of the body cavity into the luminal wall and surrounding tissue, whereas the larger particles (i.e. iron oxide particles) remain in the lumen. In yet other embodiments, in a permeable body cavity, the smaller particles (i.e. gadolinium particles) can diffuse out of the lumen of the body cavity into the luminal wall and surrounding tissue, whereas the larger particles (i.e. iron oxide particles) remain in the lumen. Because iron and gadolinium have opposite effects on magnetic resonance imaging signal intensity, once the smaller particles have diffused across the luminal surface of the body cavity, or out of the lumen of the body cavity, they can now be visualized without interference or masking by the contrast effect of the larger particles. For example, iron oxide particles reduce image signal intensity within their immediate vicinity, whereas the gadolinium particles increase signal intensity within their immediate vicinity and the result of both particles being present in the lumen of a body cavity is an overall decrease in signal intensity masking the contrast effect of the gadolinium particle. Therefore, when the lumen of a body cavity is intact and impermeable, the contrast effect of the smaller gadolinium particle is masked by the contrast effect of the larger iron particles.

In some embodiments, the relative concentrations of the T1-reducing contrast agent and T2-reducing contrast agent used may be optimized so that the concentration of the T2-reducing contrast agent (i.e. iron oxide particles) is strong enough to completely mask the effect of the T1-reducing contrast agent (i.e. gadolinium) within the lumen of a body cavity. Thus, when the body cavity is impermeable, there is virtually no signal, or image intensity, present within the lumen of the body cavity. However, when administered to a permeable body cavity, the T1-reducing contrast agent, (i.e. gadolinium chelate) is able to diffuse across the luminal surface of the body cavity, or out of the lumen of the body cavity, and escape the vicinity of the T2-reducing contrast agent (i.e. iron oxide particles), which are too large to diffuse across the luminal surface of the body cavity, or out of the lumen of the body cavity. In some embodiments, the result is that the wall of a permeable body cavity will appear as a bright ring on an MRI image, including a slice selective MRI image that includes the body cavity and surrounding tissue, whereas in the case of an impermeable body cavity, the wall of said cavity will not be visible on an MRI image, including a slice selective MRI image that includes the body cavity and surrounding tissue. In other embodiments, in the case of an impermeable body cavity, the wall of said cavity will be visible on an MRI image, including a slice selective MRI image that includes the body cavity and surrounding tissue, but will not have the bright ring enhancement of the T1-reducing contrast agent.

In various embodiments, the T1-reducing contrast agent and T2-reducing contrast agent have differing contrast effects. For example, in some embodiments, the effects of the T1-reducing contrast agent may be disambiguated from the effects of the T2-reducing contrast agent such that a person skilled in the art can detect a difference between the effects of the T1-reducing contrast agent and the T2-reducing contrast agent when viewing the results of the diagnostic imaging described herein. Different contrast effects may be visible, for example, when the T1-reducing contrast agent contains a plurality of molecules that are smaller in diameter relative to the diameter of the plurality of molecules contained in the T2-reducing contrast agent. Different contrast effects may be visible, for example, when the T1-reducing contrast agent contains a plurality of molecules that are smaller in average diameter relative to the average diameter of the plurality of molecules contained in the T2-reducing contrast agent. Different contrast effects may also be visible, for example, when the T1-reducing contrast agent affects a T1-weighted MRI image and the T2-reducing contrast agent affects a T2-weighted MRI image. In some embodiments, the T1-reducing contrast agent and the T2-reducing contrast agent have different particle sizes. In some embodiments, the T1-reducing contrast agent has a smaller particle size than the T2-reducing contrast agent. In some embodiments, the T1-reducing contrast agent has a particle size that enables it to move out of lumen of a permeable body cavity. In other embodiments, for example, the T2-reducing contrast agent contains a plurality of molecules that are smaller in diameter relative to the diameter of the plurality of molecules contained in the T1-reducing contrast agent. Different contrast effects may be visible, for example, when the T2-reducing contrast agent contains a plurality of molecules that are smaller in average diameter relative to the average diameter of the plurality of molecules contained in the T1-reducing contrast agent. In some embodiments, the T2-reducing contrast agent has a smaller particle size than the T1-reducing contrast agent. In some embodiments, the T2-reducing contrast agent has a particle size that enables it to move out of lumen of a permeable body cavity. In some embodiments, the T2-reducing contrast agent has a particle size that enables it to move out of lumen of a permeable blood vessel.

In some embodiments, the T1-reducing contrast agent exhibits predominantly T1-reducing contrast effects. In some embodiments, the T1-reducing contrast agent may also exhibit T2-reducing contrast effects. In some embodiments, the T2-reducing contrast effects of the T1-reducing contrast agent are concentration dependent. In some embodiments, the T2-reducing contrast effects of the T1-reducing contrast agent are concentration dependent. In some embodiments, the T1-reducing contrast agent may exhibit T2-reducing effects at high concentrations. In some embodiments, the T2-reducing contrast agent exhibits predominantly T2-reducing contrast effects. In some embodiments, the T2-reducing contrast agent may also exhibit T1-reducing contrast effects. In some embodiments, the T1-reducing contrast effects of the T2-reducing contrast agent are concentration dependent. In some embodiments, the T2-reducing contrast effects of the T2-reducing contrast agent are concentration dependent. In some embodiments, the T2-reducing contrast agent may exhibit T1-reducing effects at high concentrations.

In some embodiments, the T1-reducing contrast agent exhibits predominantly T1-reducing contrast effects. In some embodiments, the T1-reducing contrast agent may also exhibit T2-reducing contrast effects. In some embodiments, the T2-reducing contrast effects of the T1-reducing contrast agent are concentration dependent. In some embodiments, the T2-reducing contrast effects of the T1-reducing contrast agent are concentration dependent. In some embodiments, the T1-reducing contrast agent may exhibit T2-reducing effects at high concentrations. In some embodiments, the T2-reducing contrast agent exhibits predominantly T2-reducing contrast effects. In some embodiments, the T2-reducing contrast agent may also exhibit T1-reducing contrast effects. In some embodiments, the T1-reducing contrast effects of the T2-reducing contrast agent are concentration dependent. In some embodiments, the T2-reducing contrast effects of the T2-reducing contrast agent are concentration dependent. In some embodiments, the T2-reducing contrast agent may exhibit T1-reducing effects at high concentrations.

In some embodiments, the T1-reducing agent, the T2-reducing agent, or a combination thereof further comprises an aqueous solvent. In some embodiments, the T1-reducing contrast agent and the T2-reducing contrast agent are administered to the patient as a single composition; wherein the single composition comprises the T1-reducing contrast agent and the T2-reducing contrast agent. In some embodiments, the single composition further comprises an aqueous solvent. In some embodiments, the T1-reducing agent and the T2-reducing contrast agent are administered to the patient as two separate compositions; wherein a first composition comprises the T1-reducing contrast agent; and wherein a second composition comprises the T2-reducing contrast agent. In some embodiments, the T1-reducing agent and the T2-reducing contrast agent are administered to the patient as two separate compositions; wherein a first composition comprises the T2-reducing contrast agent; and wherein a second composition comprises the T-1 reducing contrast agent. In some embodiments, the two separate compositions each further comprise an aqueous solvent. In some embodiments, where the T1-reducing agent and the T2-reducing contrast agent are administered to the patient as two separate compositions, the separate compositions can be administered in any order including but not limited to administering the T1-reducing contrast agent followed by the T2-reducing contrast agent, administering the T2-reducing contrast agent followed by the T1-reducing contrast agent or administering the T1-reducing contrast agent and the T2-reducing contrast agent simultaneously. In some embodiments, the two separate compositions each further comprise an aqueous solvent.

In particular embodiments where the T1-reducing contrast agent and the T2-reducing contrast agent may be administered simultaneously, the T1-reducing contrast agent and the T2-reducing contrast agent may be mixed together as a dual-component solution before administration. The dual-component solution may be composed of a mixture of two MRI contrast agents: a T2-reducing contrast agent that may be a large-particle agent that reduces T2 (spin-spin relaxation time), and a T1-reducing contrast agent that may be a small-molecule agent that reduces T1 (spin-lattice relaxation time). The sizes of these two MRI contrast agents may be such that neither can pass through the lining of a healthy blood vessel, and only the relatively small T1 or T2 agent can pass through the lining of a diseased blood vessel. These two contrast agents may have opposite effects on MRI image intensity. The presence of the T2 contrast agent may reduce local image intensity by causing a more rapid nuclear spin dispersion, whereas the presence of the T1 contrast agent may increase local image intensity by allowing nuclear spins to more quickly equilibrate between phase encoding repetitions. In some embodiments, administering the dual-component solution to a healthy blood vessel may cause the blood vessel lumen to go dark (the T2 effect may mask any possible T1 effect). However, if a region of the blood vessel lining is selectively permeable to the smaller-sized T1 contrast agent, a bright signal intensity may surround the blood vessel lumen. In other embodiments, the dual-component solution may be composed of a mixture of two MRI contrast agents: a T1-reducing contrast agent that may be a large-particle agent that reduces T1 (spin-lattice relaxation time), and a T2-reducing contrast agent that may be a small-molecule agent that reduces T2 (spin-spin relaxation time). In some embodiments, administering the dual-component solution to a healthy blood vessel may cause the blood vessel lumen to go dark (the T2 effect may mask any possible T1 effect). However, if a region of the blood vessel lining is selectively permeable to the smaller-sized T2 contrast agent, a bright signal may be formed in the lumen due to diffusion of the smaller T2-reducing contrast agent into the luminal wall.

In particular embodiments where the T1-reducing contrast agent and the T2-reducing contrast agent may be administered simultaneously, the T1-reducing contrast agent and the T2-reducing contrast agent may be mixed together as a dual-component solution before administration. The dual-component solution may be composed of a mixture of two MRI contrast agents: a T2-reducing contrast agent that may be a large-particle agent that reduces T2 (spin-spin relaxation time), and a T1-reducing contrast agent that may be a small-molecule agent that reduces T1 (spin-lattice relaxation time). The sizes of these two MRI contrast agents may be such that neither can pass through the lining of a healthy urinary bladder, and only the relatively small T1 or T2 agent can pass through the lining of a diseased bladder. These two contrast agents may have opposite effects on MRI image intensity. The presence of the T2 contrast agent may reduce local image intensity by causing a more rapid nuclear spin dispersion, whereas the presence of the T1 contrast agent may increase local image intensity by allowing nuclear spins to more quickly equilibrate between phase encoding repetitions. In some embodiments, administering the dual-component solution to a healthy urinary bladder may cause the bladder lumen to go dark (the T2 effect may mask any possible T1 effect). However, if a region of the bladder lining is selectively permeable to the smaller-sized T1 contrast agent, a bright signal intensity may surround the bladder lumen. An example of this combined effect is shown in FIGS. 1A and 1B where an MRI "bladder phantom" model system was used in which membrane porosity and soft matter diffusivity of a synthetic model system can be controlled. The lumen of the bladder phantom in FIGS. 1A and 1B is dark due to the presence of the T2 contrast agent. The bladder phantom in FIG. 1A shows no permeability of the T1 contrast agent into the surrounding tissue. The permeability of the lining of the bladder phantom (FIG. 1B) is indicated by the bright signal intensity associated with the T1 contrast agent selectively diffusing through the upper bladder lining into the surrounding tissue. In other embodiments, the dual-component solution may be composed of a mixture of two MRI contrast agents: a T1-reducing contrast agent that may be a large-particle agent that reduces T1 (spin-lattice relaxation time), and a T2-reducing contrast agent that may be a small-molecule agent that reduces T2 (spin-spin relaxation time). In some embodiments, administering the dual-component solution to a healthy urinary bladder may cause the bladder lumen to go dark (the T2 effect may mask any possible T1 effect). However, if a region of the bladder lining is selectively permeable to the smaller-sized T2 contrast agent, a bright signal may be formed in the lumen due to diffusion of the smaller T2-reducing contrast agent into the luminal wall.

In some embodiments, the T1-reducing contrast agent reduces local T1 (spin-lattice relaxation) time. In some embodiments, the T2-reducing contrast agent reduces local T2 (Spin-Spin relaxation) time. In some embodiments, the T1-reducing contrast agent increases image signal intensity. In some embodiments, the T2-reducing contrast agent reduces image signal intensity.

In some embodiments, the T2-reducing contrast agent is administered in a concentration sufficient to mask the contrast effect of the T1-reducing contrast agent within the lumen of the body cavity. In some embodiments, the T2-reducing contrast agent is administered in a concentration sufficient to mask the contrast effect of the T1-reducing contrast agent within the lumen of the blood vessel.

In some embodiments, administering T1-reducing contrast agent and the T2-reducing contrast agent are completed simultaneously. In some embodiments, the T1-reducing contrast agent and the T2-reducing contrast agent may be combined into a single formulation prior to administration. In yet other embodiments, whether administered sequentially or simultaneously, the T1-reducing contrast agent and T2-reducing contrast agent may be administered as separate formulations. In some embodiments, the T1-reducing contrast agent and T2-reducing contrast agent are administered in a ratio of T1-reducing contrast agent to T2-reducing contrast agent ranging from about 1 to 100 to about 100 to 1. In some embodiments, the T1-reducing contrast agent and T2-reducing contrast agent are administered in a ratio of T1-reducing contrast agent to T2-reducing contrast agent of about 1 to about 100, about 1 to about 50, about 1 to about 25, about 1 to about 20, about 1 to about 15, about 1 to about 10, about 1 to about 5, about 1 to about 1, about 1 to about 12, or about 1 to about 11.76. In some embodiments, the ratio of the T1-reducing contrast agent to the T2-reducing contrast agent is such that the contrast effect of the T1-reducing contrast agent is masked by the contrast effect of the T2-reducing contrast agent when administered to the lumen of a body cavity. In some embodiments, the ratio of the T1-reducing contrast agent to the T2-reducing contrast agent is such that the contrast effect of the T1-reducing contrast agent is masked by the contrast effect of the T2-reducing contrast agent when administered to the lumen of a blood vessel.

In some embodiments, the T1-reducing contrast agent has a particle size that enables it to move out of lumen of a permeable body cavity. In some embodiments, the T1-reducing contrast agent has a particle size that enables it to move out of lumen of a permeable blood vessel. In some embodiments, the T1-reducing contrast agent reduces local T1 (spin-lattice relaxation) time. In some embodiments, the T2-reducing contrast agent reduces local T2 (Spin-Spin relaxation) time. In some embodiments, the T1-reducing contrast agent increases image signal intensity. In some embodiments, the T2-reducing contrast agent reduces image signal intensity. In some embodiments, the T2-reducing contrast agent is present in a concentration sufficient to mask the contrast effect of the T1-reducing contrast agent within the lumen of a body cavity. In some embodiments, the T2-reducing contrast agent is present in a concentration sufficient to mask the contrast effect of the T1-reducing contrast agent within the lumen of a blood vessel. In some embodiments, the T2-reducing contrast agent has a particle size that enables it to move out of lumen of a permeable body cavity. In some embodiments, the T2-reducing contrast agent has a particle size that enables it to move out of lumen of a permeable blood vessel.

In some embodiments, the T1-reducing contrast agent has a particle size that enables it to move out of lumen of a permeable body cavity. FIG. 3 illustrates this concept. In some embodiments, the T1-reducing contrast agent reduces local T1 (spin-lattice relaxation) time. In some embodiments, the T2-reducing contrast agent reduces local T2 (Spin-Spin relaxation) time. In some embodiments, the T1-reducing contrast agent increases image signal intensity. In some embodiments, the T2-reducing contrast agent reduces image signal intensity. In some embodiments, the T2-reducing contrast agent is present in a concentration sufficient to mask the contrast effect of the T1-reducing contrast agent within the lumen of a body cavity. In some embodiments, the T2-reducing contrast agent has a particle size that enables it to move out of lumen of a permeable body cavity.

FIG. 2 is a schematic of synthetic model system (an MRI "bladder phantom") where membrane porosity and soft matter diffusivity can be controlled. The MRI bladder phantom, shown in FIG. 2, was constructed from clear polycarbonate cylindrical tubes having an outer diameter of 35 mm, a wall thickness of 4 mm, and a length of 90 mm. A sealed (70 mm length, 7 mm diameter) segment of a filled wet dialysis membrane was suspended in the center of each polycarbonate tube lumen and aligned with the tube length, during which a liquid solution (3.125% w/w) of hydrolyzed collagen was added to the lumen of the tube (but not the lumen of the dialysis membrane) and allowed to gel. The dialysis membrane porosity was 12-14 kD MW cutoff. The bladder phantom was placed in a standard mouse MRI RF coil for imaging on a 3-Tesla bench top MRI system with a bore diameter of 160 mm and a 70 mm field of view (MR Solutions, Surrey, UK). The lumen of the dialysis membrane corresponded to the urinary bladder lumen, and was accessible via MRI-compatible vinyl tubing connected to a dosing syringe and an outlet.

Figure 5:
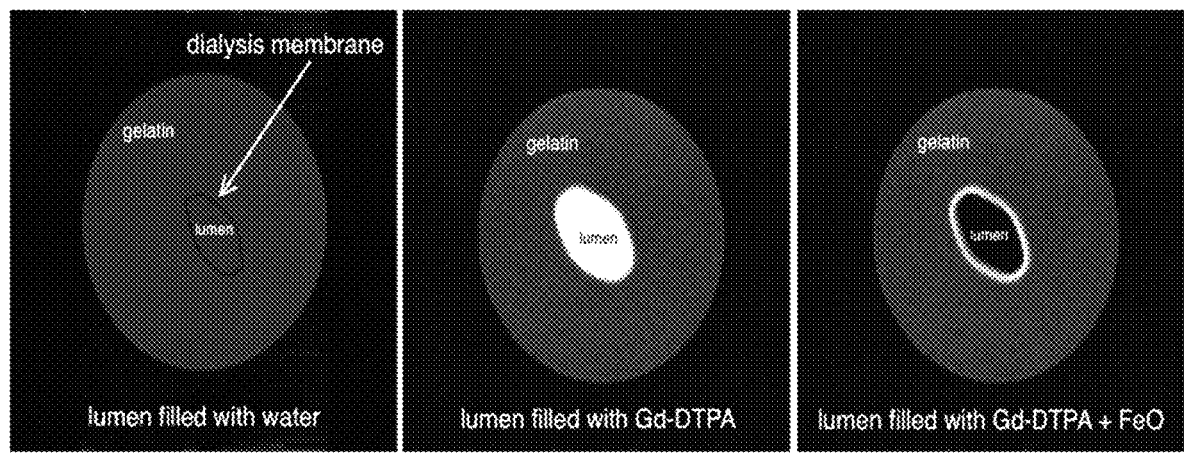
FIG. 5 is a series of MRI images of a bladder phantom system with various agents (left: water; center 425 uM gadopentetate dimeglumine (Gd-DTPA); right 425 uM Gd-DTPA and 5 mM Ferumoxytol).

FIG. 5 shows axial MRI images of a bladder phantom obtained while the lumen of the bladder phantom sequentially contained various contrast agent formulations. The left-most portion of FIG. 5 shows an axial slice spin-echo image with water in the lumen of the dialysis membrane and a fine dark line associated with the dialysis membrane is visible. This dark line is indicative of a lack of hydrogen nuclei in the liquid state where the dialysis membrane is located, a position that represents the luminal surface of the bladder. The region distal to this line, in the radial direction in composed of gelatin, which is intended to simulate the bladder wall tissue. The center image of FIG. 5 is an image of the same bladder phantom; however, in this case, the lumen is filled with 425 μM gadopentetate dimeglumine (Gd-DTPA). All three axial slice-selective spin-echo images were taken with and echo time of 60 msec and a repetition time of 600 msec. Thus these images have a combination of both T1 and T2 weighting. In the center image, the T1 weighting (the relatively short repetition time), has given rise to a bright region in the lumen associated with the presence of gadopentetate dimeglumine (Gd-DTPA). Since the entire lumen has an increased signal intensity, it is difficult to see without quantitative tools if the gadopentetate dimeglumine (Gd-DTPA) is diffusing into the gelatin an issue that becomes more relevant in a biological setting. This diffusion of the gadopentetate dimeglumine (Gd-DTPA) can be highlighted by the addition of the second contrast agent into the lumen. The result is shown in the right-most image, which is the result of adding an amount of Ferumoxytol to the lumen that resulted in a concentration of 5 mM. The particle size of Ferumoxytol was 25 nm, which was too large to diffuse across the dialysis membrane. Therefore the Ferumoxytol was able to shorten T2 of hydrogen nuclei in the vicinity of the lumen but not in the gelatin. Here we see the bright ring distally adjacent to the dialysis membrane indicating the membrane has a porosity large enough to allow gadopentetate dimeglumine (Gd-DTPA) to pass but not the Ferumoxytol.

Embodiments herein are directed to methods for measuring the permeability of a body cavity in a patient which may also be utilized to map heterogeneity in the permeability of a body cavity. In some embodiments, the body cavity is a blood vessel. In some embodiments, where only a portion of the luminal wall of a body cavity is permeable, the T1-reducing contrast agent will diffuse into the permeable region of the luminal wall of the body cavity and a signal will be generated which can then be detected and will allow for identification of the permeable region of the luminal wall. In some embodiments, the ability to map heterogeneity may have utility in detecting lesions in a body cavity. In particular embodiments, the ability to map heterogeneity may have utility in detecting diseased blood vessels. In some embodiments, diseased blood vessels may be characterized by a breakdown of the intercellular junctions of the vessel making the diseased blood vessel permeable and allowing the T1-reducing contrast agent to diffuse into the permeable region of the luminal wall of the diseased blood vessel. In some embodiments, the ability to map heterogeneity may have utility in detecting PFO, ischemic endocardium, post-embolic or pre-hemorrhagic stroke breakdown of the blood-brain-barrier (BBB), vasculitis, ruptured atherosclerotic plaque, diabetic vasculopathy, inflammation, vasculitis, autoimmune disease, infection, cancer, septic shock, or a combination thereof.

Embodiments herein are directed to methods for measuring the permeability of a body cavity in a patient which may also be utilized to map heterogeneity in the permeability of a body cavity. In some embodiments, where only a portion of the luminal wall of a body cavity is permeable, the T1-reducing contrast agent will diffuse into the permeable region of the luminal wall of the body cavity and a signal will be generated which can then be detected and will allow for identification of the permeable region of the luminal wall. In some embodiments, the ability to map heterogeneity may have utility in detecting lesions in a body cavity. In particular embodiments, the ability to map heterogeneity may have utility in detecting ulcers in the urinary bladder. In some embodiments, the ability to map heterogeneity may have utility in detecting Hunner's ulcers in the urinary bladder.

In some embodiments, imaging the patient comprises imaging via magnetic resonance imaging. Imaging the patient may generally include imaging the patient via a magnetic resonance process, such as, for example, magnetic resonance processes now known or later developed. In some embodiments, imaging the patient comprises imaging via magnetic resonance imaging. In some embodiments, imaging the patient comprises imaging via magnetic resonance imaging. However, those having ordinary skill in the art will recognize other imaging processes, such as, for example, x-ray imaging, computed tomography, positron emission scanning, and/or the like. In addition, those having ordinary skill in the art will recognize that other contrast agents, imaging agents, and/or the like, may be used alone or in combination with other contrast agents, imaging agents and/or the like to measure the permeability of a body cavity using MRI or other imaging techniques known in the art. In some embodiments, one or more contrast agents, imaging agents, and/or the like may be used if they possess a contrast effect that allows for measurement of the permeability of a body cavity. In some embodiments, imaging the patient may include imaging the patient for a period of time after administration of the T1-reducing contrast agent and the T2-reducing contrast agent. In particular embodiments, the period of time may generally be a period of time that allows for diffusion of the T1-reducing contrast agent and/or the T2-reducing contrast agent administered to the lumen of the body cavity. In some embodiments, imaging the patient is performed within about 10 minutes of administration of the T1-reducing contrast agent, T2-reducing contrast agent or combination thereof. In some embodiments, imaging the patient is performed within about 20 minutes of administration of the T1-reducing contrast agent, T2-reducing contrast agent or combination thereof. In some embodiments, imaging the patient is performed within about 30 minutes of administration of the T1-reducing contrast agent, T2-reducing contrast agent or combination thereof. In some embodiments, imaging the patient is performed within about 30 minutes of administration of the T1-reducing contrast agent, T2-reducing contrast agent or combination thereof. In some embodiments, imaging the patient is performed within about 40 minutes of administration of the T1-reducing contrast agent, T2-reducing contrast agent or combination thereof. In some embodiments, imaging the patient is performed within about 50 minutes of administration of the T1-reducing contrast agent, T2-reducing contrast agent or combination thereof. In some embodiments, imaging the patient is performed within about 60 minutes of administration of the T1-reducing contrast agent, T2-reducing contrast agent or combination thereof.

In some embodiments, the T1-reducing contrast agent may be a magnetic resonance imaging (MRI) contrast agent. In some embodiments, the first T1-reducing contrast agent comprises a gadolinium compound. In some embodiments, the gadolinium compound is selected from gadopentetate dimeglumine (Gd-DTPA), gadoterate meglumine, gadoversetamide, gadoteridol, gadodiamide, gadobenate dimeglumine, gadobutrol, gadoxetate disodium, gadofosveset trisodium and combinations thereof. Those having ordinary skill in the art will recognize that other gadolinium-containing contrast agents and/or gadolinium salts that are now known or later developed may also be used without departing from the scope of the present disclosure. In some embodiments the T1-reducing contrast agent comprises Gadopentetate dimeglumine (Gd-DTPA). In some embodiments, the Gadopentetate dimeglumine (Gd-DTPA) is present in a concentration of about 0.000425 M. In some embodiments, the gadolinium compound is encapsulated in liposomes.

In some embodiments, the T2-reducing contrast agent comprises an iron oxide. In some embodiments, the iron oxide is selected from iron (II) oxide, iron (III) oxide, ferumoxytol (Feraheme), Feraspin XS, Feraspin S, Feraspin M, Feraspin R, Feraspin L, Feraspin XL, iron nickel oxide nanopowder, iron oxide (II,III) magnetic nanoparticles, iron-nickel alloy nanopowder, magnetic iron oxide nanoparticles, carbon coated iron nanopowder, and combinations thereof. In some embodiments, the iron oxide is encapsulated in liposomes. In particular embodiments, the T2-reducing contrast agent may contain a plurality of magnetite particles. In some embodiments, the T2-reducing contrast agent comprises ferumoxytol. In some embodiments, the ferumoxytol is present in present at a concentration of about 0.005M. In some embodiments, the iron oxide is encapsulated in liposomes.

In some embodiments, the T2-reducing contrast agent may contain a plurality of molecules, where the average diameter of the molecules is about 100 A to about 1000 A. For example, the average diameter of the molecules in the T2-reducing contrast agent may be about 100 A, about 200 A, about 300 A, about 400 A, about 500 A, about 600 A, about 700 A, about 800 A, about 900 A, about 1000 A, or any value or range between any two of these values (including endpoints).

In other particular embodiments, the T1-reducing contrast agents, T2-reducing contrast agents, or a combination thereof, may include one or more of an iron oxide, iron platinum, manganese, and protein. In various embodiments, the MRI contrast agent may have an anionic neutral pH.

In some embodiments, the patient's body cavity is selected from the urinary bladder, the cardiovascular system, blood vessels, heart, lymph vessels, coelom, pericardial cavity, pericardium, intraembryonic coelom, extraembryonic coelom, chorionic cavity, dorsal cavity, ventral cavity, thoracic cavity, abdominopelvic cavity, cranial cavity, spinal cavity (or vertebral cavity), a pleural cavity, superior mediastinum, thoracic cavity, abdominal cavity, pelvic cavity, abdominopelvic cavity, kidneys, ureters, gastrointestinal tract, stomach, intestines, liver, gallbladder, pancreas, anus, reproductive system and any combination thereof.

In some embodiments, the patient's body cavity is the cardiovascular system, blood vessels, heart, or combination thereof. In some embodiments, the patient is suspected of having PFO, ischemic endocardium, post-embolic or pre-hemorrhagic stroke breakdown of the blood-brain-barrier (BBB), vasculitis, ruptured atherosclerotic plaque, diabetic vasculopathy, inflammation, vasculitis, autoimmune diseases, infection, cancer, septic shock, or a combination thereof. In some embodiments, administration of the T1-reducing contrast agent and the T2-reducing contrast agent is achieved by administration into the lumen of the cardiovascular system, blood vessels, heart, or combination thereof.

In some embodiments, the patient's body cavity is the gastrointestinal tract. In some embodiments, the patient is suspected of having a condition associated with the pathological breakdown of the layers of epithelial cells and cell junctions that line the gastrointestinal tract including but are not limited to: inflammatory bowel disease, gastric/duodenal ulcer disease, celiac disease, or a combination thereof. In some embodiments, administration of the T1-reducing contrast agent and the T2-reducing contrast agent is achieved by administration into the lumen of the gastrointestinal tract.

In some embodiments, the patient's body cavity is the urinary bladder. In some embodiments, the patient is suspected of having interstitial cystitis, bladder pain syndrome or a combination thereof. In some embodiments, administration of the T1-reducing contrast agent and the T2-reducing contrast agent is achieved by instillation into the lumen of the urinary bladder.

In some embodiments, a molecule or particle of T1-reducing contrast agents, T2-reducing contrast agents, or a combination thereof, may have a molecular weight of about 500 atomic mass units (amu) to about 1500 amu. For example, the molecule or particle may have a molecular weight of about 500 amu, about 550 amu, about 600 amu, about 650 amu, about 700 amu, about 750 amu, about 800 amu, about 850 amu, about 900 amu, about 950 amu, about 1000 amu, about 1050 amu, about 1100 amu, about 1150 amu, about 1200 amu, about 1250 amu, about 1300 amu, about 1350 amu, about 1400 amu, about 1450 amu, about 1500 amu, or any value or range between any two of these values (including endpoints). In a particular embodiment, the molecule or particle may have a molecular weight of about 938 amu.

In some embodiments, molecules or particles of the T1-reducing contrast agents, T2-reducing contrast agents, or a combination thereof, may have an average diameter of about 1 Angstrom (Å) to about 20 Å. For example the molecule may have a diameter of about 1 Å, about 2 Å, about 3 Å, about 4 Å, about 5 Å, about 6 Å, about 7 Å, about 8 Å, about 9 Å, about 10 Å, about 11 Å, about 12 Å, about 13 Å, about 14 Å, about 15 Å, about 16 Å, about 17 Å, about 18 Å, about 19 Å, about 20 Å, or any value or range between any two of these values (including endpoints).

Table 1 displays the physical characteristics of T1-reducing contrast agents suitable for use in the present invention.

TABLE 1

| Brand Name | Generic Name | Stock Concentration (M) | Molecular Weight (amu) | Average Diameter (Å) |
|---|---|---|---|---|
| Magnevist | Gadopentetate dimeglumine (Gd-DTPA) | 0.5 | 938.00 | 10 |
| Dotarem | Gadoterate meglumine | 0.5 | 753.86 | 9 |
| OptiMARK | Gadoversetamide | 0.5 | 661.77 | 8 |
| ProHance | Gadoteridol | 0.5 | 558.70 | 7 |
| Omniscan | Gadodiamide | 0.5 | 573.66 | 8 |
| MultiHance | Gadobenate Dimeglumine | 0.5 | 1058.20 | 11 |
| Gadovist | Gadobutrol | 1 | 604.70 | 8 |
| Eovist | Gadoxetate Disodium | 0.25 | 725.72 | 9 |
| Ablavar | Gadofosveset trisodium | 0.25 | 975.88 | 10 |

Table 2 displays the physical characteristics of T2-reducing contrast agents suitable for use in the present invention.

TABLE 2

| Brand Name | Generic Name | Stock Concentration of Fe (M) | Molecular Weight (amu) | Average. Diameter. (nm) |
|---|---|---|---|---|
| Feraheme | Ferumoxytol | 0.537 | n/a | 17-31 |
| FeraSpin XS | n/a | 0.01 | n/a | 10-20 |
| FeraSpin S | n/a | 0.01 | n/a | 20-30 |
| FeraSpin M | n/a | 0.01 | n/a | 30-40 |
| FeraSpin L | n/a | 0.01 | n/a | 40-50 |
| FeraSpin XL | n/a | 0.01 | n/a | 50-60 |
| FeraSpin XXL | n/a | 0.01 | n/a | 60-70 |
| FeraSpin R | n/a | 0.005 | n/a | 10-90 |
| n/a | Iron nickel oxide nanoparticle nanopowder | n/a | n/a | <50 |
| n/a | Iron oxide(II, III) magnetic nanoparticle dispersion/solution | 0.018 to 0.09 | n/a | 4-6, 9-11, or 28-32 |
| n/a | Iron oxide(II, III) magnetic nanopowder nanopowder | n/a | n/a | 4-6, 9-11, or 28-32 |
| n/a | Iron nanopowder | n/a | n/a | 25, 35-45, 40-60, or 60-80 |
| n/a | Magnetic iron oxide nanopowder | n/a | n/a | 3.5-9.5 |

Some embodiments are directed to a method for measuring the permeability of a body cavity in a patient, the method comprising: administering a contrast agent with both T1-reducing and T2-reducing effects to the patient; imaging the patient; and wherein diffusion of the solution across the luminal surface of the body cavity is indicative of permeability. In some embodiment, the body cavity is the cardiovascular system, blood vessels, heart, or a combination thereof. Some embodiments are directed to a method for measuring the permeability of a body cavity in a patient, the method comprising: imaging the patient after administering a contrast agent with both T1-reducing and T2-reducing effects to the patient; imaging the patient; and wherein diffusion of the contrast agent across the luminal surface of the body cavity is indicative of permeability. In some embodiment, the body cavity is the cardiovascular system, blood vessels, heart, or a combination thereof. In some embodiments, the contrast agent with both T1-reducing and T2-reducing effects comprises a gadolinium compound. In some embodiments, the contrast agent with both T1-reducing and T2-reducing effects may be a magnetic resonance imaging (MRI) contrast agent. In particular embodiments, the contrast agent with both T1-reducing and T2-reducing effects may be a gadolinium-containing contrast agent. In some embodiments, the gadolinium compounds include but are not limited to gadopentetate dimeglumine (Gd-DTPA), gadoterate, gadoterate meglumine, gadoversetamide, gadoteridol, gadodiamide, gadobenate dimeglumine, gadobutrol, gadoxetate disodium, gadofosveset trisodium, gadoteric acid, gadopentetate and combinations thereof. Those having ordinary skill in the art will recognize that other gadolinium-containing contrast agents and/or gadolinium salts that are now known or later developed may also be used without departing from the scope of the present disclosure. In some embodiments the solution comprises Gadopentetate dimeglumine (Gd-DTPA). In some embodiments, the Gadopentetate dimeglumine (Gd-DTPA) is present in a concentration of about 0.5 M. In some embodiments, administration of high concentrations of a contrast agent with both T1-reducing and T2-reducing effects such as, but not limited to, a gadolinium compound results in a reduction of local T1 (spin-lattice relaxation) time as well as a reduction of local T2 (Spin-Spin relaxation) time. In yet other embodiments, administration of high concentrations of a contrast agent with both T1-reducing and T2-reducing effects such as, but not limited to, a gadolinium compound results in a reduction of image signal intensity. In some embodiments, administration of high concentrations of a contrast agent with both T1-reducing and T2-reducing effects such as, but not limited to, a gadolinium compound, is sufficient to mask the contrast effect of the contrast agent with both T1-reducing and T2-reducing effects within the lumen of the body cavity. In some embodiments, masking of the contrast effect of the contrast agent with both T1-reducing and T2-reducing effects within the lumen of the body cavity indicative of a non-permeable body cavity. In yet other embodiments, diffusion of the contrast agent with both T1-reducing and T2-reducing effects across the luminal surface of the bladder, or out of the lumen of the bladder, can be visualized because of the reduction of local T2 (Spin-Spin relaxation) time and masking of the contrast effect in the lumen of the body cavity. In some embodiments, if the luminal wall of the body cavity is permeable, a bright ring will result due to diffusion of the contrast agent with both T1-reducing and T2-reducing effects into the tissue at a concentration that is lower than in the lumen of the body cavity which allows the T1-reducing effect of the contrast agent to dominate and create the bright ring image. In some embodiments, this is due to a filtering process. The contrast agent with both T1-reducing and T2-reducing effects remaining in the lumen of the body cavity remains in a concentration that is sufficiently high that the T2-reducing effect dominates and masks the signal.

Some embodiments are directed to a method for detecting the porosity of the luminal wall of a body cavity comprising: administering to the lumen of the body cavity a T1-reducing contrast agent, a T2-reducing contrast agent, wherein the particle size of the T2-reducing contrast agent are larger than the porosity of the luminal wall of the body cavity; and wherein the particle size of the T1-reducing contrast agent is smaller than the porosity of the luminal wall of the body cavity, acquiring an MRI image of the body cavity and surrounding tissue, wherein the image is acquired such that tissues and fluids having low T2 appear dark, tissues and fluids and fluids having low T1 appear bright, but however tissues and fluids having both low T1 and low T2 appear dark, and detecting if there is bright signal in said MRI image corresponding to tissue surrounding said cavity. In some embodiment, the body cavity is the cardiovascular system, blood vessels, heart, or a combination thereof.

In various embodiments, a method of performing a diagnostic examination of a patient's cardiovascular system, blood vessels, heart, or a combination thereof may include, but is not limited to, providing a T1-reducing contrast agent to the cardiovascular system, blood vessels, heart, or a combination thereof of a patient, providing a T2-reducing contrast agent to the cardiovascular system, blood vessels, heart, or a combination thereof of the patient, and imaging the patient. In some embodiments, the patient is suspected of having PFO, ischemic endocardium, post-embolic or pre-hemorrhagic stroke breakdown of the blood-brain-barrier (BBB), vasculitis, ruptured atherosclerotic plaque, diabetic vasculopathy, inflammation, vasculitis, autoimmune disease, infection, cancer, septic shock, or a combination thereof without wishing to be bound by theory, certain diseases, including, but not limited to, the conditions described herein result in a breakdown of the intercellular junctions of the blood vessel making the diseased blood vessel permeable and allowing the T1-reducing contrast agent to diffuse into the permeable region of the luminal wall of the diseased blood vessel.

In various embodiments, a method of performing a diagnostic examination of a patient's bladder may include, but is not limited to, providing a T1-reducing contrast agent to a urinary bladder of a patient, providing a T2-reducing contrast agent to the urinary bladder of the patient, and imaging the patient. In some embodiments, the patient is suspected of having interstitial cystitis, bladder pain syndrome or a combination thereof. Interstitial cystitis (IC) or bladder pain syndrome (BPS) is a multifactorial, chronic inflammatory condition of the bladder characterized by severe pelvic/perineal pain, urinary frequency and urgency affecting mostly adult women. severe pelvic/perineal pain, urinary frequency and urgency affecting mostly adult women. The etiology of IC involves an increased patency and/or porosity of a patient's urothelium relative to a urothelium of a healthy individual. Current methods of performing a diagnostic examination of a patient's bladder do not include observing and/or measuring urothelial patency and/or porosity. Currently IC/BPS is a largely incurable illness that severely compromise sexual function, ability to work, and overall quality of life. Furthermore, the economic costs of IC/BPS patients are 130% higher than those of non-IC/BPS individuals. Thus, IC/BPS is a significant health problem.

Bladder epithelium relies primarily on the presence of a surface glycosaminoglycan layer and the structural integrity of cell-cell contacts, namely tight junctions, to maintain impermeability to urinary waste. When this barrier is damaged, as in the case of IC/BPS, the leakage of urine components into the underlying bladder layers may initiate stimulation of pain fibers and the result in visceral pain symptoms.

In some embodiments, the solutions, compositions, and methods disclosed herein can be utilized with or on a subject in need of such treatment, which can also be referred to as "in need thereof." As used herein, the phrase "in need thereof means that the subject has been identified as having a need for the particular method or treatment and that the treatment has been given to the subject for that particular purpose.

In some aspects, the invention is directed to an imaging composition comprising one or more solutions, as defined herein, and, in some embodiments, a pharmaceutically acceptable carrier or diluent, or an effective amount of a pharmaceutical composition comprising a solution as defined above.

Some embodiments are directed to imaging compositions comprising: a T1-reducing contrast agent; and a T2-reducing contrast agent, wherein the T2-reducing contrast agent. In some embodiments, the imaging composition further comprises an aqueous solution. In some embodiments, the particle size of the T2-reducing contrast agent is larger than the particle size of the T1-reducing contrast agent.

In some embodiments, the T1-reducing contrast agent comprises a gadolinium compound. In some embodiments, the gadolinium compound is selected from gadopentetate dimeglumine (Gd-DTPA), gadoterate meglumine, gadoversetamide, gadoteridol, gadodiamide, gadobenate dimeglumine, gadobutrol, gadoxetate disodium, gadofosveset trisodium and combinations thereof. In some embodiments, the gadolinium compound is encapsulated in liposomes.

In some embodiments, the T2-reducing contrast agent comprises an iron oxide. In some embodiments, the iron oxide is selected from iron (II) oxide, iron (III) oxide, ferumoxytol (Feraheme), Feraspin XS, Feraspin S, Feraspin M, Feraspin R, Feraspin L, Feraspin XL, iron nickel oxide nanopowder, iron oxide (II,III) magnetic nanoparticles, iron-nickel alloy nanopowder, magnetic iron oxide nanoparticles, carbon coated iron nanopowder, and combinations thereof. In some embodiments, the iron oxide is encapsulated in liposomes.

In some embodiments, the methods and compositions described herein may comprise other contrast agents that when administered together, or alone, exhibit a contrast effect that allows measurement of the permeability of a body cavity. In some embodiments, these contrast agents may be useful for measuring body cavity permeability using MRI as well as imaging techniques other than MRI.

The contrast agents and compositions of the present invention can be administered in the conventional manner by any route where they are active. Administration can be systemic, topical, or oral or via instillation. For example, administration can be, but is not limited to, parenteral, subcutaneous, intravenous, intramuscular, intraperitoneal, transdermal, oral, buccal, or ocular routes, or intravaginally, by inhalation, by depot injections, or by implants. Thus, modes of administration for the compositions and solutions of the present invention (either alone or in combination with other pharmaceuticals) can be, but are not limited to, instillation, sublingual, injectable (including short-acting, depot, implant and pellet forms injected subcutaneously or intramuscularly), or by use of vaginal creams, suppositories, pessaries, vaginal rings, rectal suppositories, intrauterine devices, and transdermal forms such as patches and creams.

Specific modes of administration will depend on the indication or body cavity being imaged. The selection of the specific route of administration and concentration of imaging compositions containing the T1-reducing contrast agents, T2-reducing contrast agents, or combinations thereof, is to be adjusted or titrated by the clinician according to methods known to the clinician in order to optimize the imaging process. The concentration to be administered will depend on the characteristics of the patient to which the contrast agent, contrast agents, or compositions being administered, e.g., the particular patient (human or animal) treated, age, weight, health, types of concurrent treatment, if any, and frequency of treatments, and can be easily determined by one of skill in the art (e.g., by the clinician).

Imaging compositions containing the T1-reducing contrast agents, T2-reducing contrast agents, or combinations thereof, of the present invention and a suitable carrier can be solid dosage forms which include, but are not limited to, tablets, capsules, cachets, pellets, pills, powders and granules; topical dosage forms which include, but are not limited to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder; comprising an effective amount of a polymer or copolymer of the present invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Gilman's The Pharmaceutical Basis of Therapeutics*, 6th Edition, MacMillan Publishing Co., New York (1980) can be consulted.

Imaging compositions containing the T1-reducing contrast agents, T2-reducing contrast agents, or combinations thereof, can be formulated for instillation. The agents and compositions can be administered by instillation over a period of about 15 minutes to about 24 hours. Formulations for instillation can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

Imaging compositions containing the T1-reducing contrast agents, T2-reducing contrast agents, or combinations thereof, can be formulated for parenteral administration by injection, e.g., by bolus injection or continuous infusion. The agents and compositions can be administered by continuous infusion subcutaneously over a period of about 15 minutes to about 24 hours. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

For oral administration, the Imaging compositions containing the T1-reducing contrast agents, T2-reducing contrast agents, or combinations thereof, can be formulated readily by combining the agents described herein with pharmaceutically acceptable carriers well known in the art. Such carriers enable the agents of the invention to be formulated as tablets, pills, dragees, capsules, liquids, gels, syrups, slurries, suspensions and the like, for oral ingestion by a patient to be treated. Imaging preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active doses.

Imaging compositions containing the T1-reducing contrast agents, T2-reducing contrast agents, or combinations thereof, which can be used orally include, but are not limited to, push-fit capsules made of gelatin, as well as soft, sealed capsules made of gelatin and a plasticizer, such as glycerol or sorbitol. The push-fit capsules can contain the agents in admixture with filler such as, e.g., lactose, binders such as, e.g., starches, and/or lubricants such as, e.g., talc or magnesium stearate and, optionally, stabilizers. In soft capsules, the agents can be dissolved or suspended in suitable liquids, such as fatty oils, liquid paraffin, or liquid polyethylene glycols. In addition, stabilizers can be added. All formulations for oral administration should be in dosages suitable for such administration. For buccal administration, the solutions can take the form of, e.g., tablets or lozenges formulated in a conventional manner.

For administration by inhalation, the Imaging compositions containing the T1-reducing contrast agents, T2-reducing contrast agents, or combinations thereof, for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

Imaging compositions containing the T1-reducing contrast agents, T2-reducing contrast agents, or combinations thereof, of the present invention can also be formulated in rectal compositions such as suppositories or retention enemas, e.g., containing conventional suppository bases such as cocoa butter or other glycerides.

In some embodiments, the Imaging compositions containing the T1-reducing contrast agents, T2-reducing contrast agents, or combinations thereof, may be prepared as suspensions, solutions or emulsions in oily or aqueous vehicles suitable for injection. In such embodiments, such solutions may further include formulatory agents such as suspending, stabilizing and or dispersing agents formulated for parenteral administration. Such injectable solutions may be administered by any route, for example, instillation, subcutaneous, intravenous, intramuscular, intra-arterial or bolus injection or continuous infusion, and in embodiments in which injectable compositions are administered by continuous infusion, such infusion may be carried out for a period of about 15 minutes to about hours. In certain embodiments, compositions for injection may be presented in unit dosage form, e.g., in ampoules or in multi-dose containers, with an added preservative.

In some embodiments, the Imaging compositions containing the T1-reducing contrast agents, T2-reducing contrast agents, or combinations thereof, described herein may be encapsulated in liposomes. The liposomes may be used to increase the size of the agents. The liposomes may be prepared by a variety of methods. In the process of making liposomes, the agents may be added at any desired time. For example, agents may be associated with components of liposomes before liposomes are formed. Agents may be combined with liposome components at the time the liposomes are made. Agents may also be added after the liposomes are formed. Other methods of associating agents with liposomes may exist. Generally, agents which are hydrophilic in nature may be located or associated with the internal cavity of the liposome particles. Agents which are lipophilic in nature may be located or associated with the lipid bilayer of liposome particles. Generally, the agents herein are located or associated with the internal cavity of the liposome.

There are a variety of methods for encapsulating the Imaging compositions containing the T1-reducing contrast agents, T2-reducing contrast agents, or combinations thereof, described herein into the liposomes. The method may include selecting one or more agents to be used. The method may also include forming liposomes in the presence of the one or more agents. In some embodiments, these methods may include hydration of dried lipids, introduction of a volatile organic solution of lipids into an aqueous solution causing evaporation of the organic solution, dialysis of an aqueous solution of lipids and detergents or surfactants to remove the detergents or surfactants, and others. In some embodiments, the agents encapsulated in liposomes may be manufactured by co-dissolving sphingomyelin with the agent in a 30% tertiary butyl alcohol-water solvent then lyophilized. This procedure will generate a pre-liposomal lyophilate of the agent with particle sizes that range from about 1 µm to about 50 µm diameters. Upon rehydration, a standard multiple dialysis technique will be used to isolate specific size ranges of the agents encapsulated in the liposomes.

In addition to the formulations described herein, the Imaging compositions containing the T1-reducing contrast agents, T2-reducing contrast agents, or combinations thereof, of the present invention can also be formulated as a depot preparation. Such long acting formulations can be administered by implantation (for example subcutaneously or intramuscularly) or by intramuscular injection.

Depot injections can be administered at about 1 to about 6 months or longer intervals. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

In transdermal administration, the compounds of the present invention, for example, can be applied to a plaster, or can be applied by transdermal, therapeutic systems that are consequently supplied to the organism.

Imaging compositions containing the T1-reducing contrast agents, T2-reducing contrast agents, or combinations thereof, described herein also can comprise suitable solid or gel phase carriers or excipients. Examples of such carriers or excipients include but are not limited to calcium carbonate, calcium phosphate, various sugars, starches, cellulose derivatives, gelatin, and polymers such as, e.g., polyethylene glycols.

The Imaging compositions containing the T1-reducing contrast agents, T1-reducing contrast agents, or combinations thereof, of the present invention can also be formulated and/or administered in combination with other active ingredients, such as, for example, adjuvants, protease inhibitors, or other compatible drugs or compounds where such combination is seen to be desirable or advantageous in achieving the desired effects of the methods described herein.

Although the present invention has been described in considerable detail with reference to certain preferred embodiments thereof, other versions are possible. Therefore the spirit and scope of the appended claims should not be limited to the description and the preferred versions contained within this specification.

EXAMPLES

Example 1: MRI Contrast Agent Formulation in a Model Bladder System with Known Permeability To confirm proof-of-concept of the MRI permeability assay, applicants have tested the concept in both an in-vitro setting where membrane porosity and soft matter diffusivity of a synthetic model system can be controlled (a MRI "bladder phantom").

The MRI bladder phantom was constructed from clear polycarbonate cylindrical tubes having an outer diameter of 35 mm, a wall thickness of 4 mm, and a length of 90 mm. A sealed (70 mm length, 7 mm diameter) segment of a filled wet dialysis membrane was suspended in the center of each polycarbonate tube lumen and aligned with the tube length, during which a liquid solution (3.125% w/w) of hydrolyzed collagen was added to the lumen of the tube (but not the lumen of the dialysis membrane) and allowed to gel. The dialysis membrane pore size was 12-14 kDa MWCO. Approximately half of the dialysis membrane, in a direction along its axis, was occluded so that the imaging technique could distinguish between regions of permeability and impermeability within the same image. The phantom was placed in a standard mouse MRI RF coil for imaging on a 3-Tesla bench top MRI system with a bore diameter of 160 mm and a 70 mm field of view (MR Solutions, Surrey, UK). The lumen of each dialysis membrane corresponds to the urinary bladder lumen, and was be accessible via MRI-compatible vinyl tubing connected to a dosing syringe and an outlet.

Axial MRI images of the phantom were obtained while the lumen contained a contrast agent formulation composed of 425 uM Gd-DTPA and 5 mM Ferumoxytol. A standard 90°-180° spin-echo pulse sequence was used along with standard frequency and phase encodings. The echo times (TE) and repetition times (TR) were 60 msec and 600 msec respectively to obtain T1 weighted images. A diagram of the phantom is illustrated in FIG. 2, and the resulting axial (cross sectional) image is shown in FIG. 1B. FIG. 1B, illustrates the bright region (corresponding to the remaining permeable region of the dialysis membrane) where the gadolinium component of the contrast agent formulation was able to escape the vicinity of the larger iron oxide particles constituting the T2 reducing component.

Example 2: In Vivo Mouse Model of Interstitial Cystitis

Normal mice were examined by MRI to establish baseline MRI imaging parameters, determine the appropriate volume of administered solution and also optimize protamine sulfate-induced bladder cystitis and test the same imaging parameters in damaged bladders. MRI imaging was performed on a 3-Tesla bench top MRI system. Animals were anesthetized and maintained on a heated Minerve animal bed and animal gating and monitoring was performed by an MR-compatible system on the MRI system.

The mouse provides a lower urinary tract similar to humans and the C56BL/6 strain are readily available and known to be free from known predispositions to genitourinary tract abnormalities. Female mice were used for their shorter urethra compared to male counterparts. C57BL/6 mice were used in particular because a significant database for this strain is available and it is the most common strain utilized in medical research. All animals were sourced from Charles River Laboratories.

Each animal was imaged individually, the solution administered to the bladder was comprised of sterile H2O to establish that the administered solution alone has no effect on the bladder imaging. Following confirmation of this, the solution administered to the bladder was comprised of a T2 contrast agent to observe the three dimensional shape of the bladder lining when full. Gadolinium-based T1 contrast agents were then added to determine whether the different agents can diffuse into the surrounding tissue from a healthy bladder.

Following validation of normal bladder imaging, mice underwent bladder-lining damage through the application of protamine sulfate. Cystitis was induced by direct instillation of 10 mg/ml protamine sulfate.

Isoflurane-inhaled anesthesia was used and pre-emptive analgesia using Buprenex 0.01-0.05 mg/kg intramuscular (IM) injection was administered prior to anesthetic induction for solution administration to the bladder and imaging procedures. Before each procedure, the animal was observed to rule out any contraindications and its weight was recorded. Each animal was initially anesthetized by placing it in a tank flooded with isoflurane and oxygen (4% Isoflurane and oxygen delivered at 4 liters per minute). Following induction, the animal was maintained under anesthesia (1-2% isoflurane at 0.5 L/min) for the duration of the solution administration and imaging, typically 0.25-1.5 hours.

A volume of 0.1 ml of either sterile water or contrast agent was slowly administered via a 24 gauge sterile polyurethane catheter, lubricated with a 2% lidocaine gel. This administration was maintained for at least 30 minutes during MRI imaging sequences, after which the bladders were manually drained and rinsed with saline. During imaging, the animal's respiration and body temperature were monitored quantitatively via an on-board respiratory and temperature monitor. The duration of each MRI sequences varied from as little as 3 minutes up to 20 minutes. Following imaging, each animal was removed from the MRI animal bed and recovered in a clean, contained area that is heated. All animals were visually monitored during recovery. After the animal fully recovered, it was returned to a clean filter-top cage.

Figure 4:
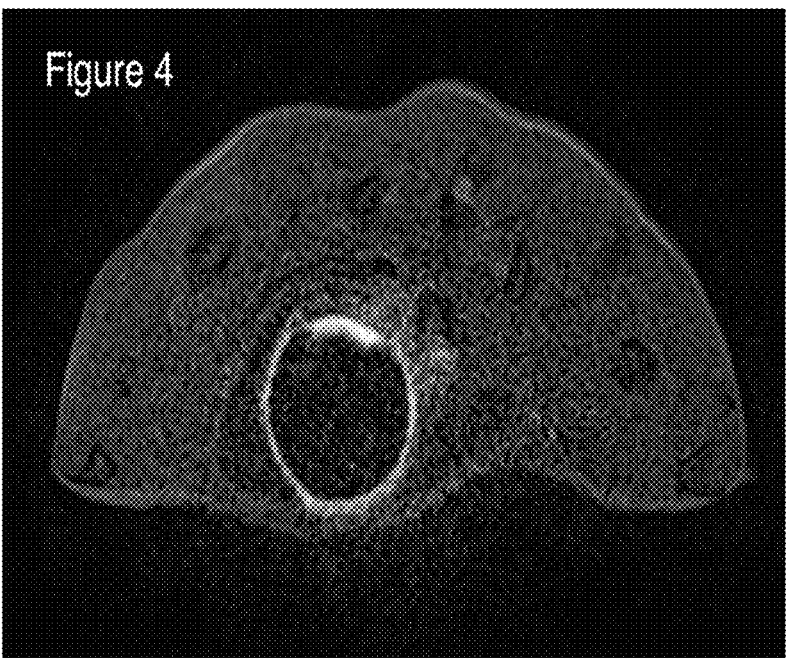
FIG. 4 is an MRI image of the axial cross section of a mouse with chemically induced bladder permeability to which a dual-contrast agent formulation has been administered.

The resulting image using the same axial spin-echo pulse sequence (TE=60 msec, TR=600 msec) is shown in FIG. 4. Note that a fat suppression techniques was employed to eliminate most of the signal associated with adipose tissue surrounding the urinary bladder. Some signal from adipose tissue remains in the upper left region from the bladder. However, the important feature to notice in FIG. 4 is the bright ring structure surrounding the bladder, which is the circular structure in the bottom center of the image. The dark center of the circle is the lumen of the mouse's urinary bladder filled with the contrast agent formulation. The white ring at the periphery of the full bladder corresponds to the thin bladder wall within which the gadolinium has selectively diffused escaping the vicinity of the Feraheme (iron oxide). If the T2 contrast agent penetrates the bladder lining in the disease model of the mouse and/or the T1 contrast agent penetrates the bladder lining of the normal mouse, contrast agents encapsulated in liposomes will be used.

What is claimed:

1. A method for measuring permeability of a body cavity in a patient comprising:
    administering a composition comprising a T1-reducing contrast agent and a T2-reducing contrast agent directly into or onto the body cavity of the patient;
    imaging the body cavity in the patient, the body cavity comprising a lumen and a luminal surface, the lumen having the T1-reducing contrast agent and the T2-reducing contrast agent; and
    determining diffusion of the T1-reducing contrast agent from the lumen of the body cavity across the luminal surface of the body cavity,
    wherein diffusion of the T1-reducing contrast agent across the luminal surface of the body cavity is indicative of permeability of the body cavity associated with pathologic breakdown of one or more layers of the body cavity,
wherein the T2-reducing contrast agent is retained within the lumen, and
wherein the body cavity is urinary bladder or ureters.

2. The method of claim 1, wherein the composition further comprises an aqueous solvent.

3. The method of claim 1, wherein imaging the patient comprises imaging via magnetic resonance imaging.

4. The method of claim 1, wherein imaging the patient is performed within about 10 minutes of administration of the composition.

5. The method of claim 1, wherein the T1-reducing contrast agent comprises a gadolinium compound.

6. The method of claim 5, wherein the gadolinium compound is selected from the group consisting of gadopentetate dimeglumine (Gd-DTPA), gadoterate meglumine, gadoversetamide, gadoteridol, gadodiamide, gadobenate dimeglumine, gadobutrol, gadoxetate disodium, gadofosveset trisodium, and combinations thereof.

7. The method of claim 5, wherein the gadolinium compound is encapsulated in liposomes.

8. The method of claim 1, wherein the T2-reducing contrast agent comprises an iron oxide.

9. The method of claim 1, wherein the iron oxide is selected from the group consisting of iron (II) oxide, iron (III) oxide, ferumoxytol, iron nickel oxide nanopowder, iron oxide (II,III) magnetic nanoparticles, iron-nickel alloy nanopowder, magnetic iron oxide nanoparticles, carbon coated iron nanopowder, and combinations thereof.

10. The method of claim 8, wherein the iron oxide is encapsulated in liposomes.

11. The method of claim 1, wherein the body cavity in the patient is the urinary bladder.

12. The method of claim 11, wherein the patient is suspected of having interstitial cystitis, bladder pain syndrome, or a combination thereof.

13. The method of claim 11, wherein administration of the composition is achieved by instillation into the lumen of the urinary bladder.

14. A method for measuring permeability of a body cavity in a patient comprising:
imaging the body cavity in the patient after administering a composition comprising a T1-reducing contrast agent and a T2-reducing contrast agent directly into or onto the body cavity of the patient, the body cavity comprising a lumen and a luminal surface, the lumen having the T1-reducing contrast agent and the T2-reducing contrast agent; and
determining diffusion of the T1-reducing contrast agent from the lumen of the body cavity across the luminal surface of the body cavity,
wherein diffusion of the T1-reducing contrast agent across the luminal surface of the body cavity is indicative of permeability of the body cavity associated with pathologic breakdown of one or more layers of the body cavity,
wherein the T2-reducing contrast agent is retained within the lumen, and
wherein the body cavity in the patient is urinary bladder or ureters.

15. The method of claim 14, wherein the composition further comprises an aqueous solvent.

16. The method of claim 14, wherein imaging the patient comprises imaging via magnetic resonance imaging.

17. The method of claim 14, wherein imaging the patient is performed within about 10 minutes of administration of the composition.

18. The method of claim 14, wherein the T1-reducing contrast agent comprises a gadolinium compound.

19. The method of claim 18, wherein the gadolinium compound is selected from the group consisting of gadopentetate dimeglumine (Gd-DTPA), gadoterate meglumine, gadoversetamide, gadoteridol, gadodiamide, gadobenate dimeglumine, gadobutrol, gadoxetate disodium, gadofosveset trisodium, and combinations thereof.

20. The method of claim 19, wherein the gadolinium compound is encapsulated in liposomes.

21. The method of claim 14, wherein the T2-reducing contrast agent comprises an iron oxide.

22. The method of claim 21, wherein the iron oxide is selected from the group consisting of iron (II) oxide, iron (III) oxide, ferumoxytol, iron nickel oxide nanopowder, iron oxide (II,III) magnetic nanoparticles, iron-nickel alloy nanopowder, magnetic iron oxide nanoparticles, carbon coated iron nanopowder, and combinations thereof.

23. The method of claim 21, wherein the iron oxide is encapsulated in liposomes.

24. The method of claim 14, wherein the body cavity in the patient is the urinary bladder.

25. The method of claim 24, wherein the patient is suspected of having interstitial cystitis, bladder pain syndrome, or a combination thereof.

26. The method of claim 25, wherein administration of the composition is achieved by injection, instillation, catheterization, infusion, or a combination thereof into the lumen of the urinary bladder.

27. The method of claim 1, wherein the composition comprises a concentration of the T2-reducing contrast agent configured to completely mask a contrast effect of the T1-reducing contrast agent in the composition.

28. The method of claim 14, wherein the composition comprises a concentration of the T2-reducing contrast agent configured to completely mask a contrast effect of the T1-reducing contrast agent in the composition.

29. The method of claim 1, wherein the T2-reducing contrast agent has an average particle diameter from about 3.5 microns to about 80 microns,
wherein the luminal surface is impermeable to the T2-reducing contrast agent such that the T2-reducing contrast agent is retained within the lumen.

30. The method of claim 29, wherein the T1-reducing contrast agent has an average particle diameter less than the average particle diameter of the T2-reducing contrast agent.

31. The method of claim 14, wherein the T2-reducing contrast agent has an average particle diameter from about 3.5 microns to about 80 microns,
wherein the luminal surface is impermeable to the T2-reducing contrast agent such that the T2-reducing contrast agent is retained within the lumen.

32. The method of claim 31, wherein the T1-reducing contrast agent has an average particle diameter less than the average particle diameter of the T2-reducing contrast agent.

33. The method of claim 1, wherein administration of the composition is achieved by instillation.

34. The method of claim 1, wherein the composition is administered through a natural opening to the body cavity.

35. The method of claim 1, wherein the composition is administered orally.

36. The method of claim 14, wherein administration of the composition is achieved by instillation.

37. The method of claim 14, wherein the composition is administered through a natural opening to the body cavity.

38. The method of claim 14, wherein the composition is administered orally.

39. The method of claim 1, wherein the body cavity in the patient is the ureters.

40. The method of claim 14, wherein the body cavity in the patient is the ureters.

* * * * *